United States Patent
Karas et al.

(10) Patent No.: US 12,016,595 B2
(45) Date of Patent: Jun. 25, 2024

(54) POLY-AXIAL PEDICLE SCREW ASSEMBLY AND PACKAGING THEREFOR

(71) Applicant: Spinal Balance, Inc., Holland, OH (US)

(72) Inventors: Arthur Sotere Karas, Copley, OH (US); Christian Ferdinand Ludwig Schultz, Augsburg (DE)

(73) Assignee: Spinal Balance, Inc., Toledo, OH (US)

( * ) Notice: Subject to any disclaimer, the term of this patent is extended or adjusted under 35 U.S.C. 154(b) by 0 days.

(21) Appl. No.: 15/036,965

(22) PCT Filed: Nov. 24, 2014

(86) PCT No.: PCT/US2014/067059
§ 371 (c)(1),
(2) Date: May 16, 2016

(87) PCT Pub. No.: WO2015/077690
PCT Pub. Date: May 28, 2015

(65) Prior Publication Data
US 2016/0287293 A1    Oct. 6, 2016

Related U.S. Application Data

(60) Provisional application No. 61/907,419, filed on Nov. 22, 2013.

(51) Int. Cl.
*A61B 17/70* (2006.01)
*A61B 17/86* (2006.01)
(Continued)

(52) U.S. Cl.
CPC ...... *A61B 17/7037* (2013.01); *A61B 17/7032* (2013.01); *A61B 17/7082* (2013.01);
(Continued)

(58) Field of Classification Search
CPC ............ A61B 17/7032; A61B 17/7037; A61B 17/7035; A61B 2017/564; A61B 17/865;
(Continued)

(56) References Cited

U.S. PATENT DOCUMENTS 4,671,410 A * 6/1987 Hansson ............... A61F 2/0095
206/438
5,538,428 A * 7/1996 Staubli ................ A61C 8/0089
206/63.5
(Continued)

FOREIGN PATENT DOCUMENTS

CN    1241127 A    1/2000
CN    2510023 Y    9/2002
(Continued)

OTHER PUBLICATIONS

Extended European Search Report, Application No. 14863695.4, dated Sep. 27, 2017.
(Continued)

*Primary Examiner* — Eduardo C Robert
*Assistant Examiner* — Tara Rose E Carter
(74) *Attorney, Agent, or Firm* — MacMillan, Sobanski & Todd, LLC

(57) ABSTRACT

A pedicle screw assembly including a pedicle screw, a tulip head, a set screw, and a washer; a packaging assembly for a pedicle screw; a pedicle screw screwdriver assembly; and a set packaging assembly are disclosed.

14 Claims, 19 Drawing Sheets

(51) Int. Cl.
| | |
|---|---|
| *A61B 50/00* | (2016.01) |
| *A61B 50/30* | (2016.01) |
| *B65D 25/04* | (2006.01) |
| *B65D 25/14* | (2006.01) |
| *B65D 47/32* | (2006.01) |
| *B65D 51/28* | (2006.01) |

(52) U.S. Cl.
CPC ...... *A61B 17/7091* (2013.01); *A61B 17/8625* (2013.01); *A61B 17/865* (2013.01); *B65D 25/04* (2013.01); *B65D 25/14* (2013.01); *B65D 47/32* (2013.01); *B65D 51/28* (2013.01); *A61B 2050/005* (2016.02); *A61B 2050/3008* (2016.02)

(58) Field of Classification Search
CPC ...... A61B 2050/005; A61B 2050/3008; A61B 50/30
USPC .................................................. 606/250–279
See application file for complete search history.

(56) References Cited

U.S. PATENT DOCUMENTS

| | | | | |
|---|---|---|---|---|
| 5,738,685 | A | 4/1998 | Halm et al. | |
| 5,755,575 | A * | 5/1998 | Biggs | A61C 8/0087 206/63.5 |
| 5,996,779 | A * | 12/1999 | Klardie | A61C 8/0087 206/63.5 |
| 6,217,332 | B1 * | 4/2001 | Kumar | A61C 8/0087 206/368 |
| 7,214,227 | B2 * | 5/2007 | Colleran | A61B 17/7032 606/273 |
| 8,021,397 | B2 | 9/2011 | Farris et al. | |
| 8,075,599 | B2 * | 12/2011 | Johnson | A61B 17/7037 606/266 |
| 9,060,811 | B2 | 6/2015 | Werner et al. | |
| 9,750,579 | B2 | 9/2017 | Richart | |
| 2004/0043358 | A1 * | 3/2004 | Howlett | A61C 8/0087 433/141 |
| 2006/0243616 | A1 * | 11/2006 | Caron | A61B 50/30 206/349 |
| 2006/0271047 | A1 * | 11/2006 | Jackson | A61B 17/7037 606/270 |
| 2007/0123870 | A1 | 5/2007 | Jeon et al. | |
| 2007/0161996 | A1 * | 7/2007 | Biedermann | A61B 17/7037 606/305 |
| 2007/0270839 | A1 | 11/2007 | Jeon et al. | |
| 2008/0015580 | A1 * | 1/2008 | Chao | A61B 17/7037 606/86 A |
| 2009/0266890 | A1 * | 10/2009 | Bagozzi | A61L 2/07 235/385 |
| 2010/0023061 | A1 * | 1/2010 | Randol | A61B 17/7037 606/278 |
| 2010/0145394 | A1 * | 6/2010 | Harvey | A61B 17/7032 606/302 |
| 2010/0211114 | A1 | 8/2010 | Jackson | |
| 2010/0241175 | A1 * | 9/2010 | Walker | A61B 17/8605 606/305 |
| 2010/0318136 | A1 * | 12/2010 | Jackson | A61B 17/7037 606/305 |
| 2012/0010661 | A1 * | 1/2012 | Farris | A61B 17/7037 606/264 |
| 2012/0123486 | A1 | 5/2012 | Werner et al. | |
| 2012/0271365 | A1 * | 10/2012 | Daubs | A61B 17/7086 606/86 A |
| 2013/0000262 | A1 * | 1/2013 | Richart | A61B 17/865 53/492 |
| 2013/0013003 | A1 * | 1/2013 | Carbone | A61B 17/863 606/305 |
| 2013/0018428 | A1 * | 1/2013 | Harper | A61B 17/7056 606/305 |
| 2013/0190821 | A1 * | 7/2013 | Marik | A61B 17/7022 606/263 |
| 2014/0127645 | A1 * | 5/2014 | Goldenberg | A61C 8/0089 433/174 |
| 2014/0188175 | A1 * | 7/2014 | Mishra | A61B 17/7082 606/279 |

FOREIGN PATENT DOCUMENTS

| | | |
|---|---|---|
| CN | 101252888 A | 8/2008 |
| CN | 101612057 A | 12/2009 |
| CN | 102525625 A | 7/2012 |
| DE | 9421989 U1 | 7/1997 |
| DE | 102009052838 A1 | 5/2011 |
| FR | 2854143 A1 | 10/2004 |
| FR | 2959216 A1 | 10/2011 |
| FR | 2974290 A1 | 10/2012 |
| JP | 2007502677 A | 2/2007 |
| JP | 2012105981 A | 6/2012 |
| JP | 2016537140 A | 12/2016 |

OTHER PUBLICATIONS

Expended European Search Report, Application No. 18158703.1, dated Jun. 19, 2018.
CN First Office Action, Application No. 201480071527.1, dated Sep. 5, 2018.
JP Office Action, Application No. 2016-533662, dated Aug. 28, 2018.
CN Second Office Action, Application No. 201480071527.1, dated Jun. 27, 2019.
Indian Examination Report Under Sections 12 & 13, Application No. 201647020796, dated Feb. 15, 2020.
Japanese Office Action, Application No. 2019205206, dated Dec. 2, 2020.
Korean Office Action, Application No. 10-2016-7015677, dated Apr. 27, 2021.

* cited by examiner

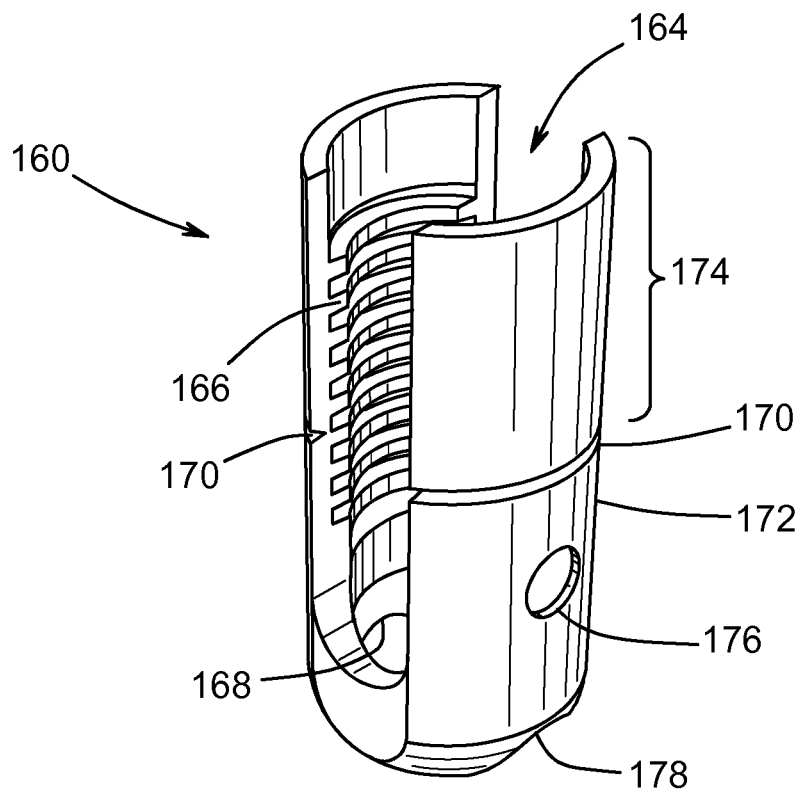
FIG. 4A
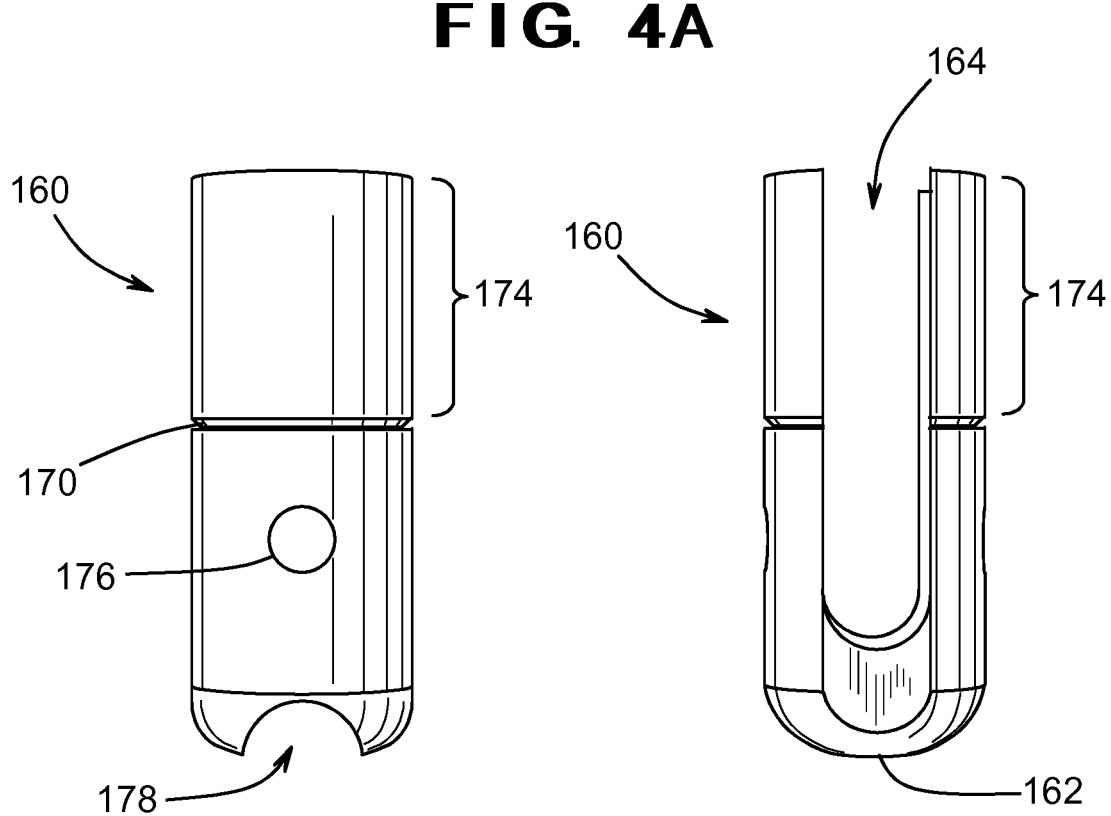
FIG. 4B  FIG. 4C

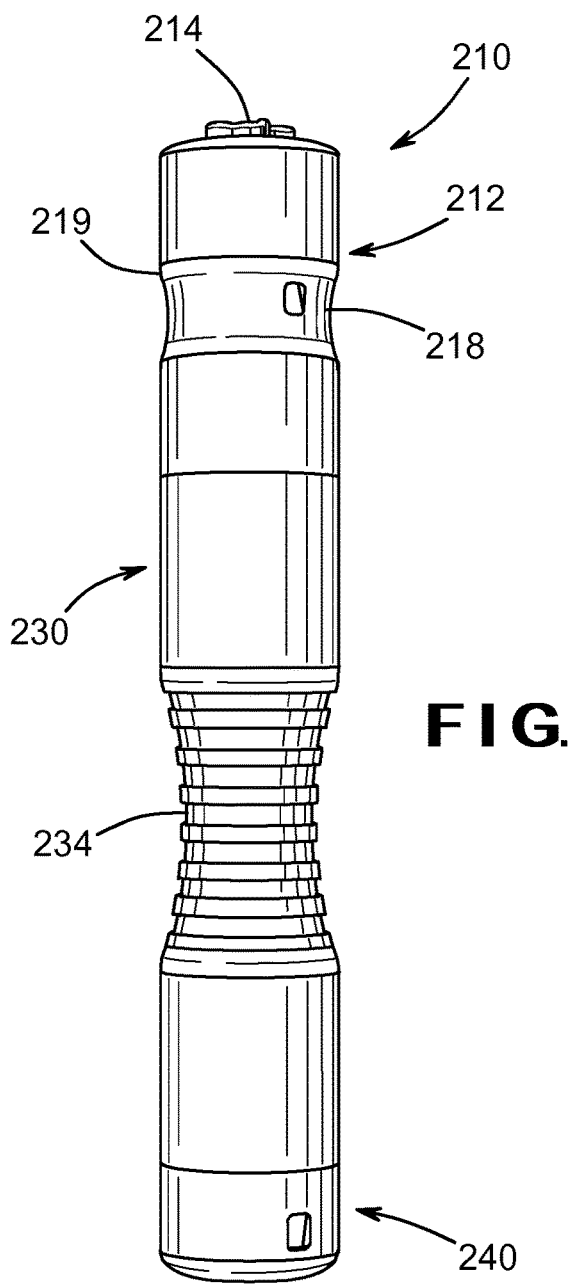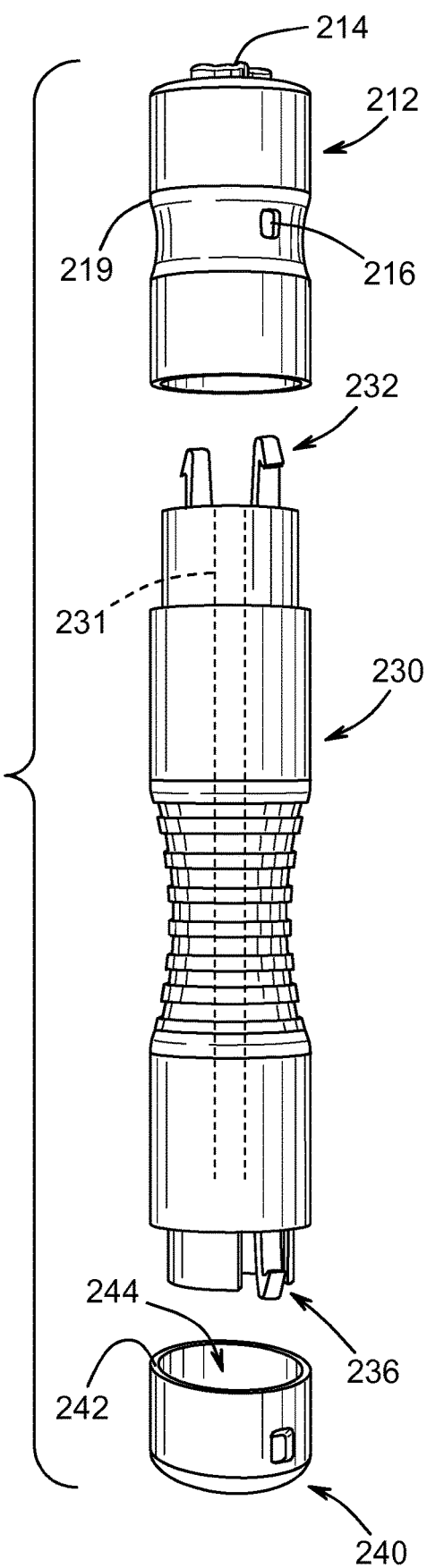
FIG. 9A
FIG. 9B

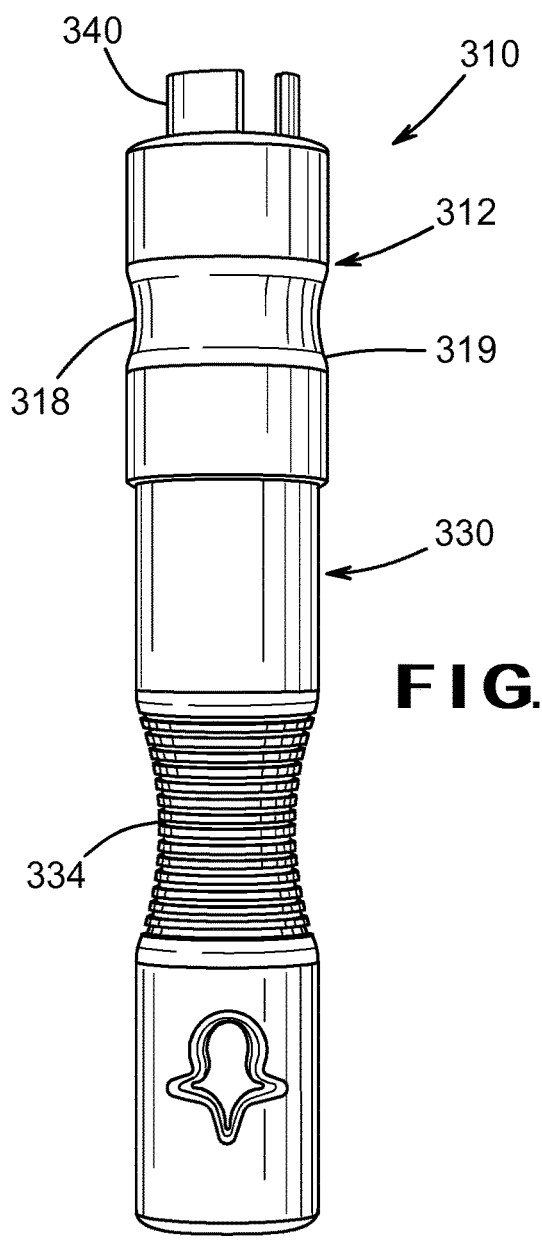
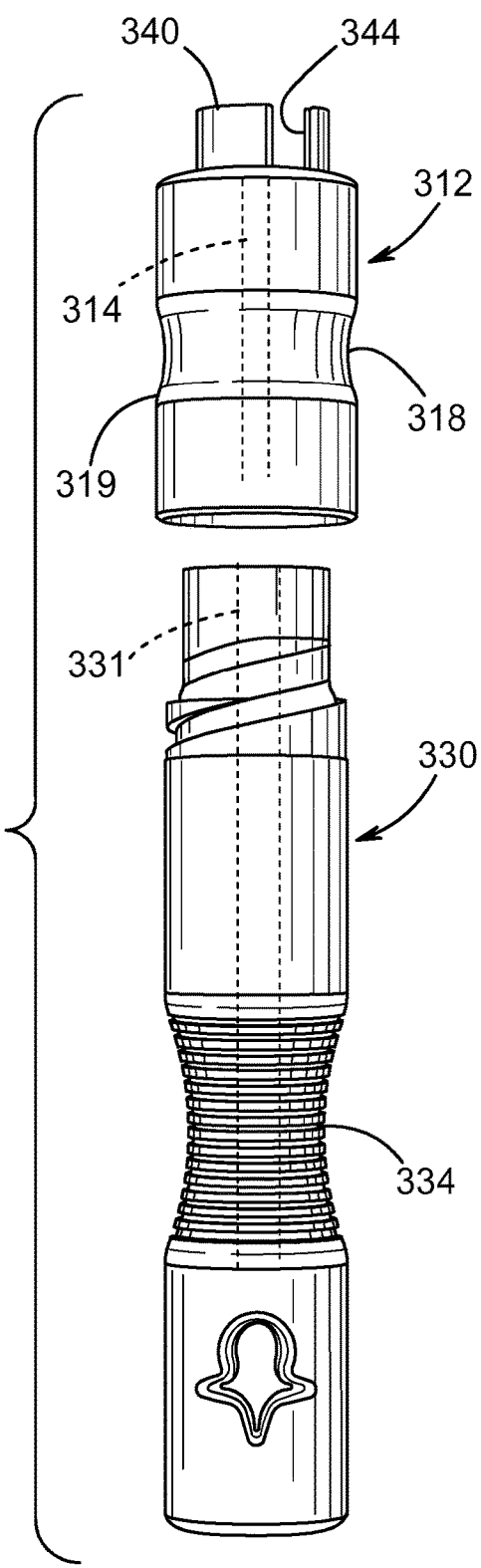
FIG. 10A
FIG. 10B

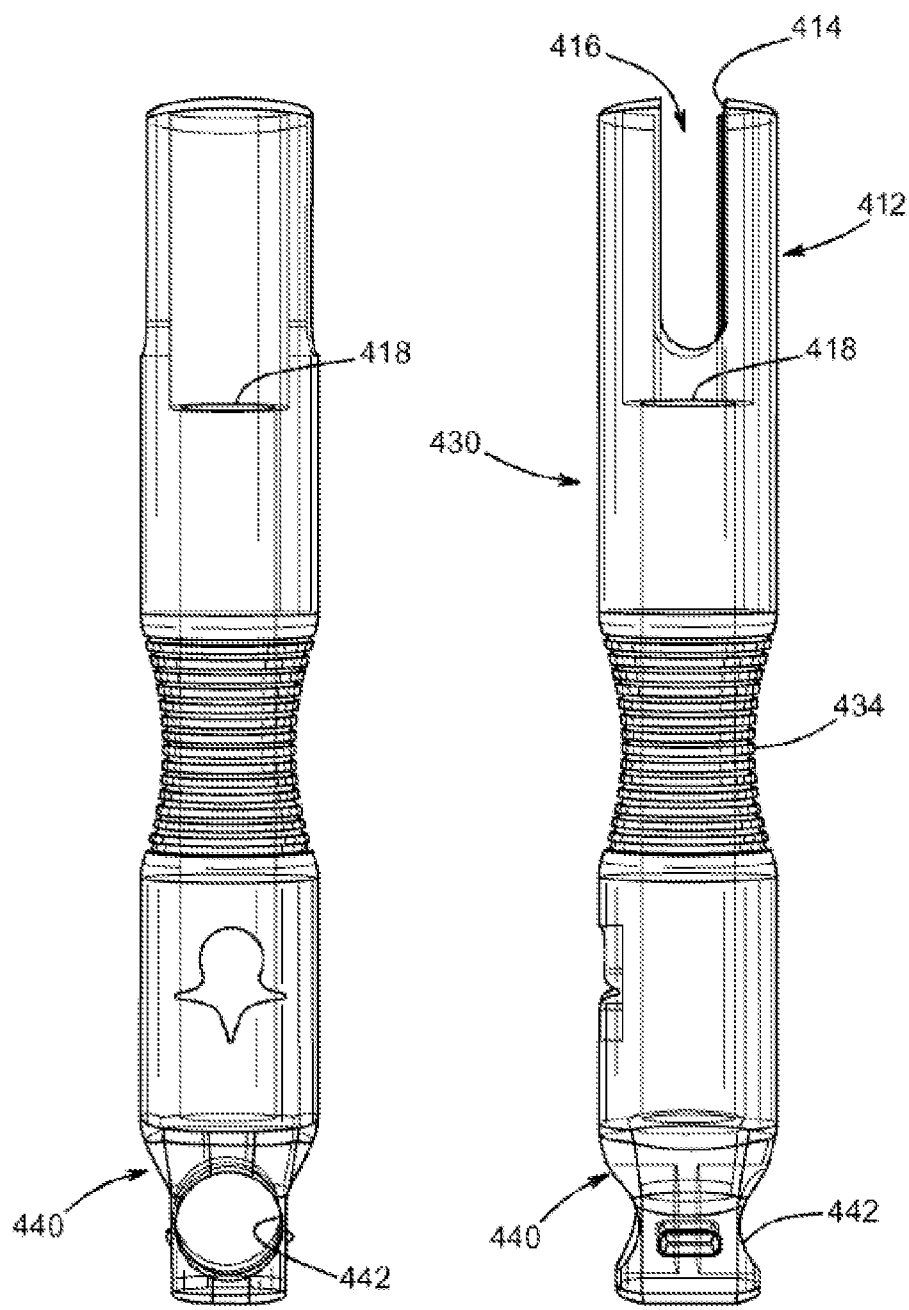

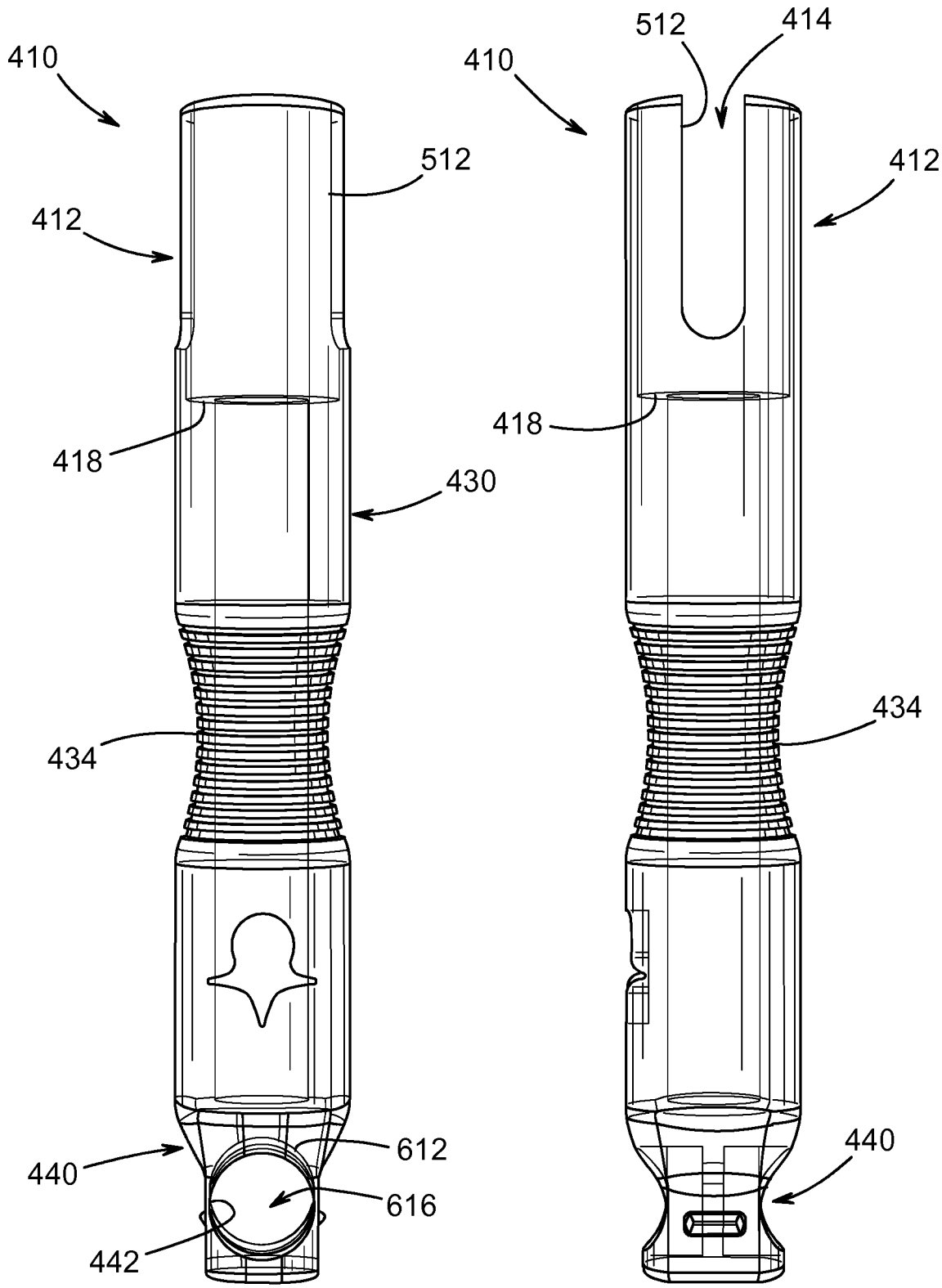
F I G. 12A          F I G. 12B

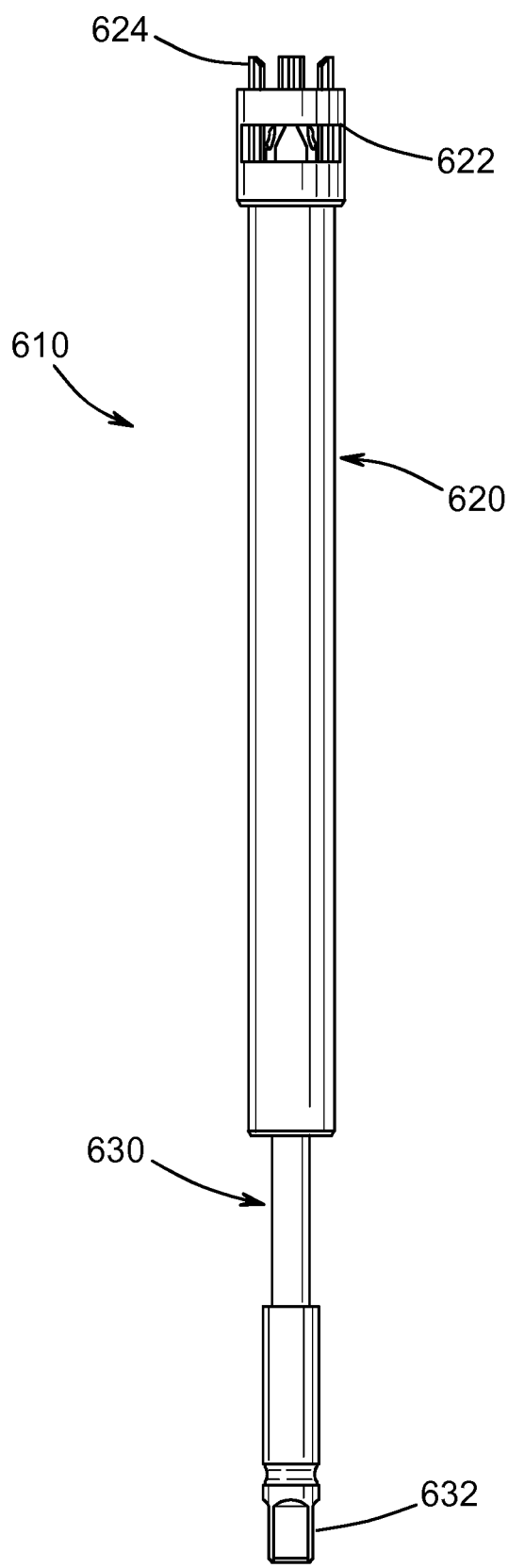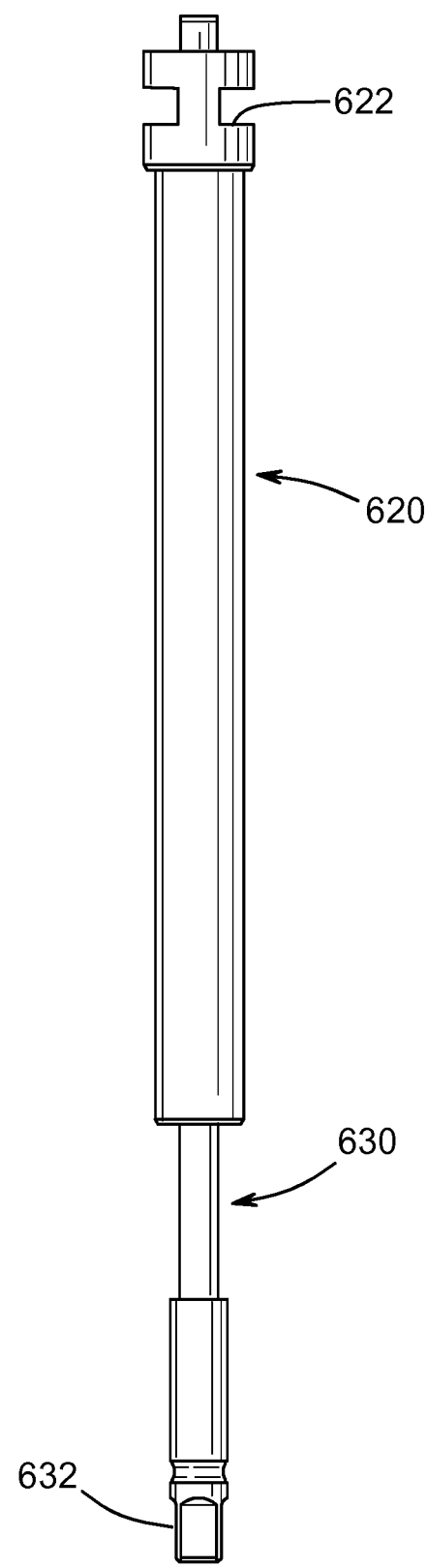
FIG. 14A  FIG. 14B

POLY-AXIAL PEDICLE SCREW ASSEMBLY AND PACKAGING THEREFOR

CROSS-REFERENCE TO RELATED APPLICATIONS

This application is the National Phase of International Application PCT/US2014/067059 filed Nov. 24, 2014, which designated the U.S. That International Application was published in English under PCT Article 21(2) on May 28, 2015 as International Publication Number WO 2015/077690A1. PCT/US2014/067059 claims priority to U.S. Provisional Application No. 61/907,419 filed Nov. 22, 2013. The disclosures of both applications are incorporated herein by reference.

BACKGROUND OF THE INVENTION

Spinal fixation can be used to treat scoliosis, spondylolisthesis, degenerative disc disease, vertebra fractures, and other spinal disorders or abnormalities such as abnormal curvature. Spinal fixation devices provide rigidity to spinal segments by mechanically immobilizing them. In some devices, pedicles connect the vertebral body to the posterior elements.

Generally, a pedicle screw has a threaded shaft and slots at the head. Screws are screwed into the spine through the respective pedicles of two or more vertebral levels and a rod is used to lock the screws in place to minimize relative motion. The rod is then locked into place with a fastening screw. The fixation can be either on one side or both sides of the vertebra. However, if the top portion of the device cannot rotate, the surgeon is forced to change the orientation of the entire screw in order to properly place the rod in the slots. This leads to screw loosening problems. There is thus a need for poly-axial screws that are able to rotate, allowing the surgeon to properly insert the screw and place the rod accordingly while only having to change the orientation of the screw head.

SUMMARY OF THE INVENTION

Provided herein is a pedicle screw assembly having a pedicle screw, a tulip head, a set screw, and a washer. The pedicle screw has a threaded shaft and a knurled head. The tulip head has a channel configured to receive a rod, opposing walls with threaded inner surfaces, and a bottom opening configured to receive the shaft of the pedicle screw. The set screw has threaded outer walls capable of engaging the threaded inner surfaces of the opposing walls of the tulip head. The washer has a semi-circular opening configured to receive a rod and a knurled inner surface configured to engage the knurled head of the pedicle screw. In use, the pedicle screw shaft is inserted through the opening of the tulip head and driven into a vertebral bone; the washer is positioned within the tulip head such that the knurled inner surface engages the knurled head of the pedicle screw; a rod is inserted into the channel; and the set screw is threaded through the inner surfaces toward the washer such that the rod is locked in the semi-circular opening of the washer. In certain embodiments, the washer further comprises an extrusion configured to lock the washer in place relative to the tulip head. In certain embodiments, the tulip head further comprises a cut on an outer surface of the opposing walls. In certain embodiments, the shaft further comprises cuts configured to allow the pedicle screw to be self-tapping. In certain embodiments, the shaft is cannulated. In certain embodiments, the opposing walls of the tulip head have threaded outer surfaces.

Further provided herein is a pedicle screw packaging assembly that includes a cap, a body, and a bottom compartment. The cap defines a top channel and has a curvature and a knurled outer cap surface. The body defines a middle channel and has a curvature and a knurled outer body surface. The body is configured to receive a pedicle screw in an upright position. The bottom compartment is connected to the body and defines a bottom channel configured to receive a set screw. The cap and body are configured to connect together. In certain embodiments, the cap comprises a hole configured to allow gas to enter the packaging assembly. In certain embodiments, the cap and body, when connected, are removable by application of external pulling forces in directions opposite each other. In certain embodiments, the bottom compartment is disposed between the cap and the body, and the bottom compartment and the cap are configured to be connected together.

Further provided herein is a pedicle screw screwdriver assembly that has a sleeve and a driver. The sleeve has a top end and a bottom end, and defines an elongated channel that defines an axis. The bottom end has a plurality of wings. The driver has a head end and a screw end, the screw end comprising an extrusion configured to engage an opening of a tulip head, and the driver being disposed within the channel. The driver can freely move within the channel along the axis without any rotation relative to the sleeve. In certain embodiments, the driver further comprises an extrusion on an outer surface, the extrusion being configured to engage an opening in the sleeve so as to prevent the driver from rotating relative to the sleeve. In certain embodiments, the driver comprises a head end shape configured to match a standard surgical ratcheting handle.

Further provided herein is a set screw screwdriver assembly having a sleeve and a driver. The sleeve has a top end and a bottom end, the top end comprising a plurality of wings configured to grip a set screw, and the sleeve defining a channel that defines an axis. The driver has a head end and a screw end, the head end having a geometric extrusion configured to engage a set screw. The driver is disposed within the channel, and can freely move within the channel along the axis without any rotation relative to the sleeve. In certain embodiments, the sleeve comprises cuts configured to engage a tulip head.

Various aspects of this invention will become apparent to those skilled in the art from the following detailed description of the preferred embodiment, when read in light of the accompanying drawings.

BRIEF DESCRIPTION OF THE DRAWINGS

FIG. 4A shows an isometric view of another embodiment of a tulip head of a pedicle screw assembly.

FIG. 4B shows a side view of the tulip head shown in FIG. 4A.

FIG. 4C shows a front view of the tulip head shown in FIG. 4A.

FIG. 9A shows a front view of another embodiment of a 3-part packaging assembly having a span lock mechanism.

FIG. 9B shows a trimetric (or, unassembled) view of the packaging assembly of FIG. 9A.

FIG. 10A shows a front view of an embodiment of a 2-part packaging assembly.

FIG. 10B shows a trimetric (or, unassembled) view of the packaging assembly of FIG. 10A.

FIG. 11C shows a front view of the packaging assembly of FIG. 11A. In this view, the parts are holographic to see a better view of the inner workings.

FIG. 11D shows a side view of the packaging assembly of FIG. 11B. In this view, the parts are holographic to see a better view of the inner workings.

FIG. 12A shows a sectional view of another embodiment of a 1-part packaging assembly having sleeve inserts. In this view, the parts are holographic to see a better view of the inner workings.

FIG. 12B shows a side view of the packaging assembly of FIG. 12A.

FIG. 14A shows an isometric view of a set screw screwdriver assembly.

FIG. 14B shows a side view of a set screw screwdriver assembly.

DETAILED DESCRIPTION OF THE PREFERRED EMBODIMENT

Various embodiments are described in the present disclosure in the context of spinal fixation assemblies. Those of ordinary skill in the art will realize that the following detailed description of the embodiments is illustrative only and not intended to be in any way limiting. Other embodiments will readily suggest themselves to such skilled persons having the benefit of this disclosure. Reference to an "embodiment," "aspect," or "example" in this disclosure indicates that the embodiments of the invention so described may include a particular feature, structure, or characteristic, but not every embodiment necessarily includes the particular feature, structure, or characteristic. Further, repeated use of the phrase "in one embodiment" does not necessarily refer to the same embodiment, although it may.

For convenience, certain terms employed in the specification, examples, and appended claims are collected here, before further description of the invention. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used to refer to one or to more than one (i.e., to at least one) of the grammatical object of the article. By way of example, "an element" means one element or more than one element.

The term "plurality" means more than one.

The terms "comprise" and "comprising" are used in the inclusive, open sense, meaning that additional elements may be included.

The term "including" is used to mean "including but not limited to, "including" and "including but not limited to" are used interchangeably.

Provided herein is a spinal fixation assembly that includes a pedicle screw assembly, a pedicle screw packaging assembly, a pedicle screw screwdriver assembly, and a set screw screwdriver assembly.

Pedicle Screw Assembly

Figure 7A:
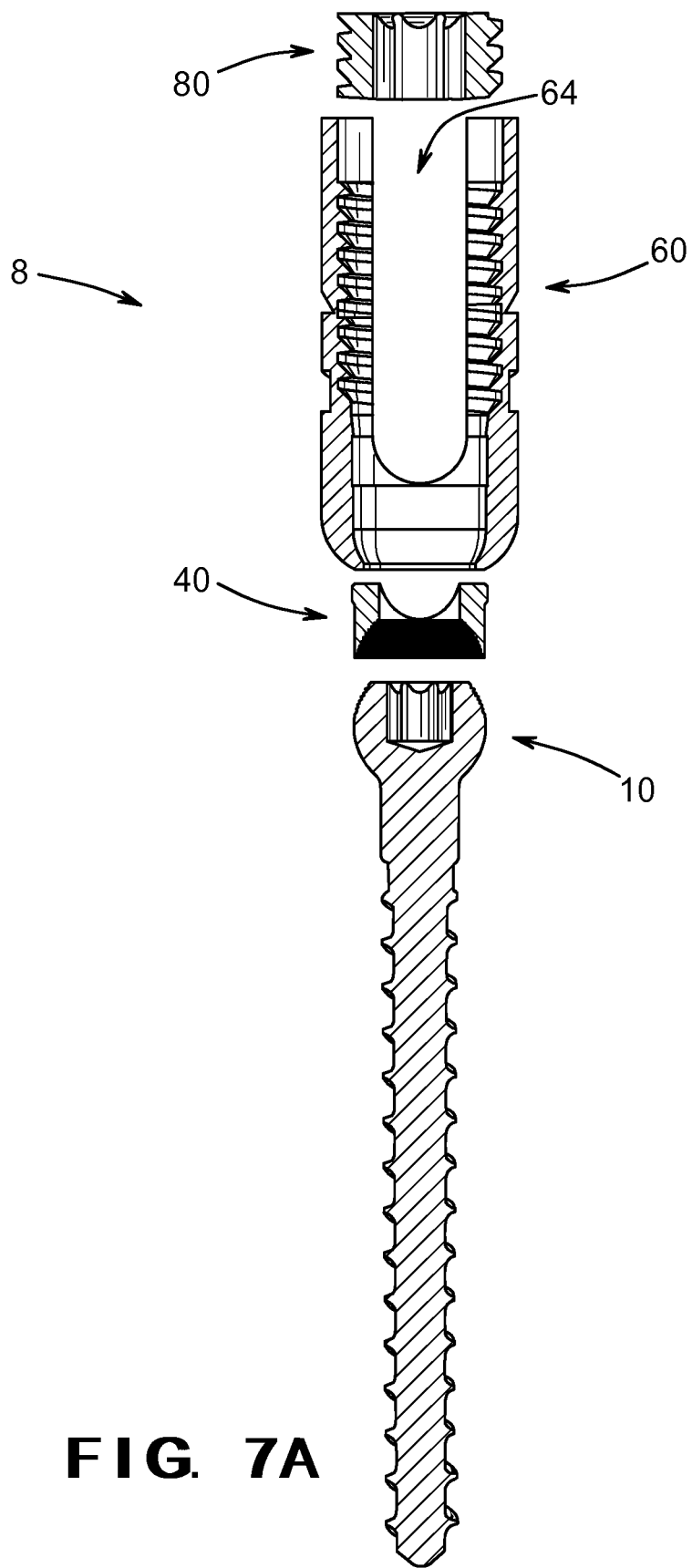
FIG. 7A shows a sectional view of a pedicle screw assembly with a pedicle screw extending through an opening at a bottom of a tulip head, a washer locking the pedicle screw in place in the tulip head, and a set screw engaging the threaded inside walls of the tulip head.
Figure 7B:
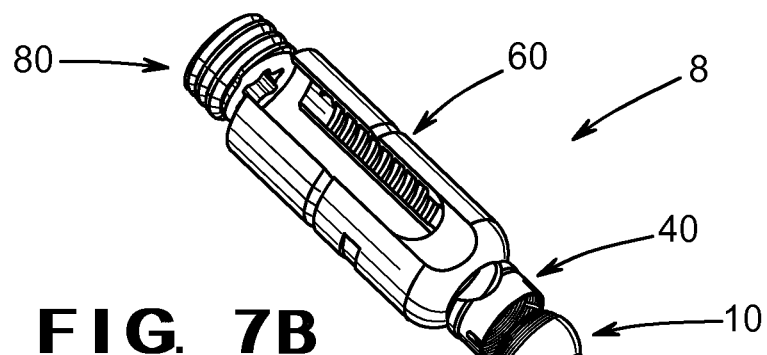
FIG. 7B shows an isometric view of the pedicle screw assembly of FIG. 7A.
Figure 7C:
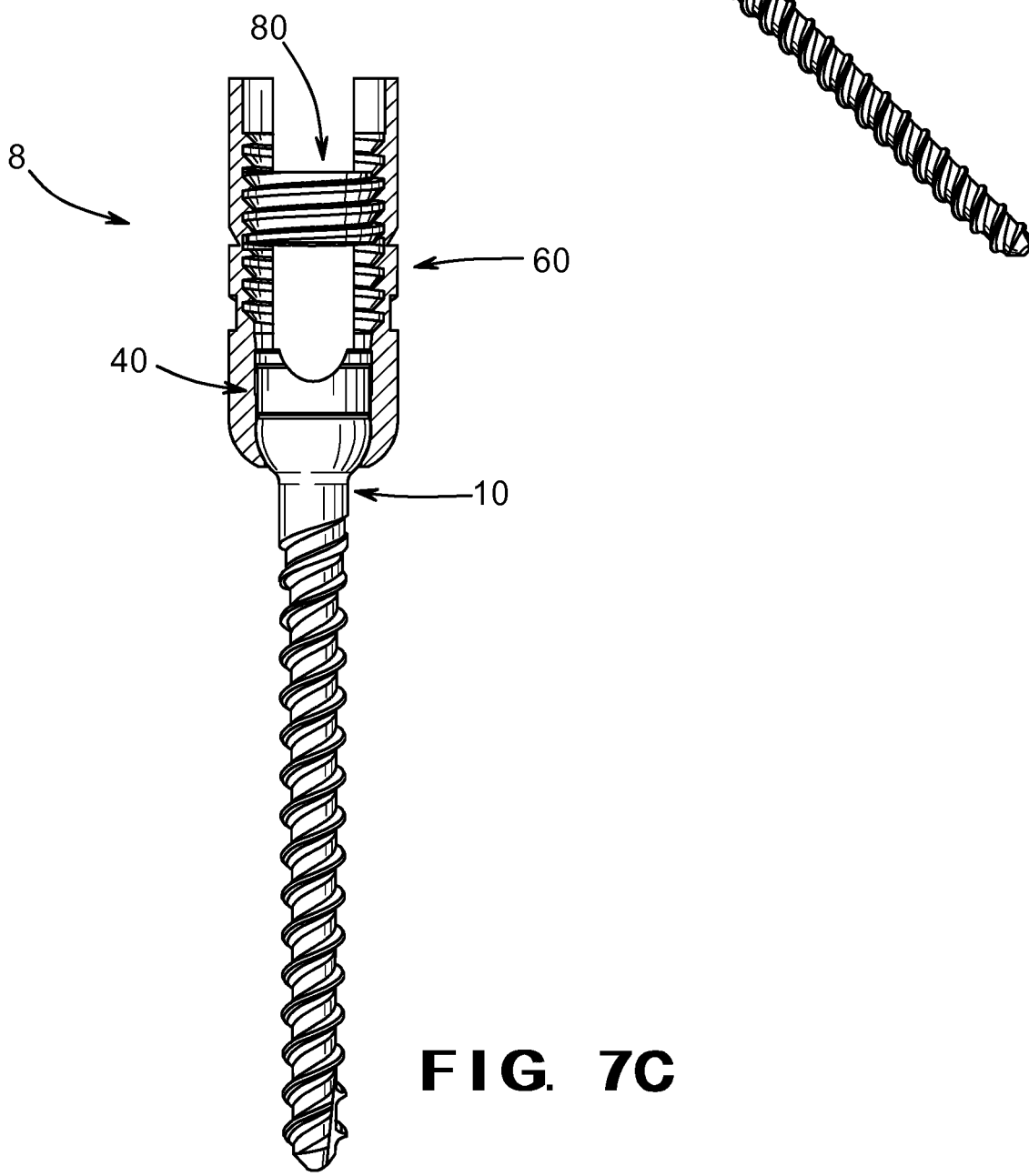
FIG. 7C shows a front view of the pedicle screw assembly. In this view, the tulip head is transparent to view the washer within the tulip head.

Referring first to FIGS. 7A-7C to show an overall concept, an assembled pedicle screw assembly 8 comprises a pedicle screw 10, a washer 40, a tulip head 60, and a set screw 80. The washer 40 sits on top of a pedicle screw head 16 in the assembly 8. The pedicle screw head 16 is positioned at a of the tulip head 60. The tulip head has a bottom opening 68 for passage of a pedicle screw shaft 12. During use of such pedicle screw assembly (e.g., once a vertebral rod is in place in the patient), the set screw 40 is used to compress the rod onto the washer 40, which causes the washer 40 to compress on the pedicle screw head 16, and thereby lock the pedicle screw shaft 12 in place. As further explained herein, when inserted into a patient, this locking in place in the patient removes the poly-axial feature of the assembly 8. The set screw 80 and tulip head 60 function to hold the rod securely in place.

Figure 1A:
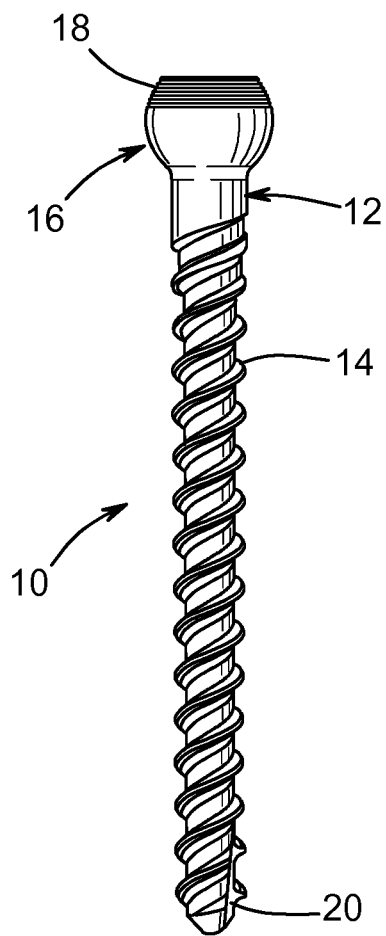
FIG. 1A shows a front view of a poly-axial pedicle screw.

FIGS. 1A-1D show various views of the pedicle screw 10. As seen in FIG. 1A, the pedicle screw 10 has an elongated, narrow body, or shaft, 12 that has threads 14. The top of the shaft 14 has a partially spherical head 16. In certain embodiments, a portion of the head 16 has a knurled surface 18 for proper gripping with the washer 40. In certain embodiments, a bottom part of the shaft 12 has one or more cuts 20 along the shaft 12, which allow for the pedicle screw 10 to be self-tapping.

The shaft 12 can vary in diameter, length, and thread type. The diameter and length of the shaft are variable to accommodate the size of the patient's vertebra. A larger vertebra would generally call for a greater shaft diameter and length, and a smaller vertebra would generally call for a smaller shaft diameter and length. The shaft can also be cannulated through a central axis. Cannulation allows for the surgeon to map the trajectory of the screw placement. The shaft can also be fenestrated to insert cement through the cannulation. Cement injection provides for a stronger grip between the screw and bone.

Figure 1B:
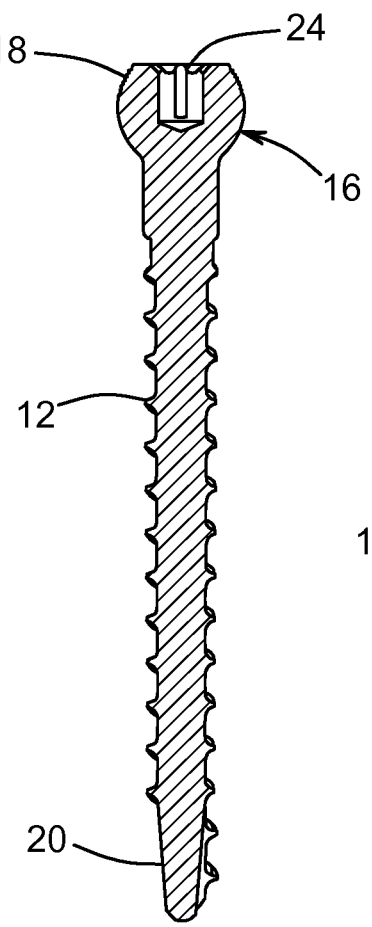
FIG. 1B shows a sectional view of a poly-axial pedicle screw.
Figure 1C:
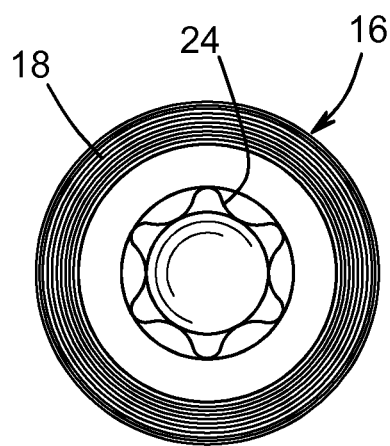
FIG. 1c shows a top view of a poly-axial pedicle screw.

As seen in FIGS. 1B and 1C, the shaft 12 can have a hex-shaped groove 24. The groove 24 is used to insert the pedicle screw 10 into the patient's bone with the use of a suitable hex head screwdriver. Alternative geometries, such as a tori or flower shape, are also possible for the groove 24 and corresponding screwdriver.

Figure 1D:
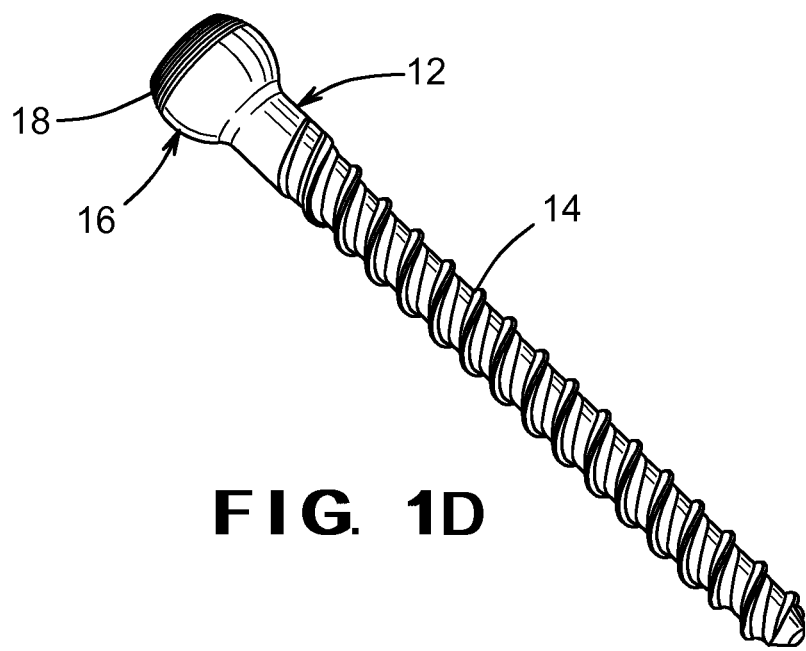
FIG. 1D shows an isometric view of a poly-axial pedicle screw.
Figure 2A:
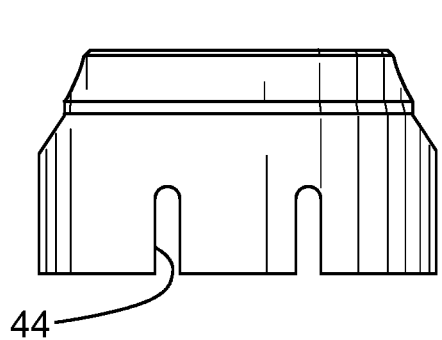
FIG. 2A shows a front view of a washer of a pedicle screw assembly.
Figure 2B:
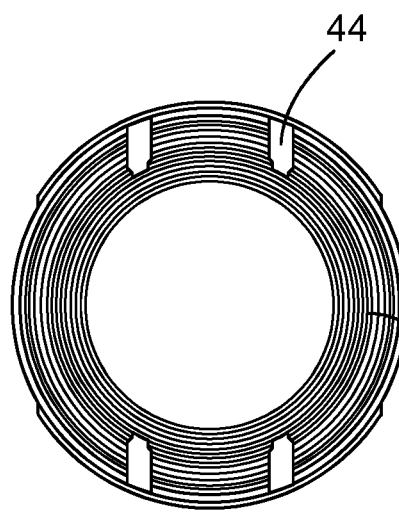
FIG. 2B shows a top view of a washer of a pedicle screw assembly.
Figure 2C:
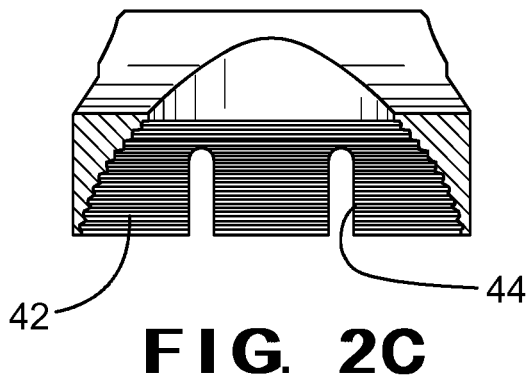
FIG. 2C shows a sectional view of a washer of a pedicle screw assembly.
Figure 2D:
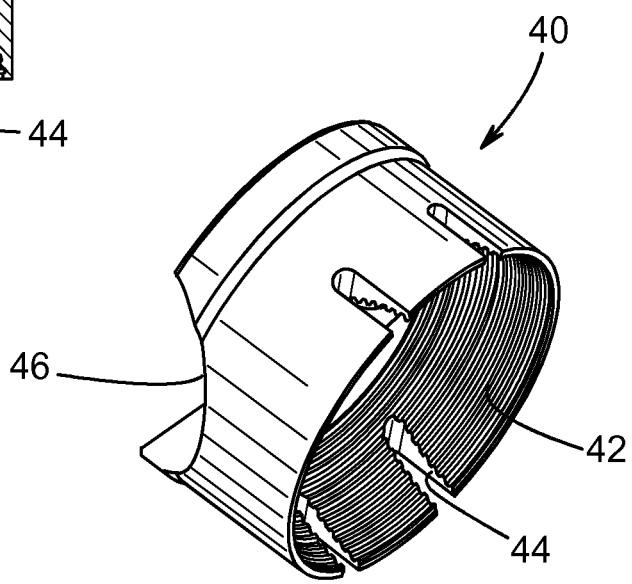
FIG. 2D shows an isometric view of a washer of a pedicle screw assembly.

As seen in FIGS. 1C-1D, the threads 14 on the shaft 12 are spiral. The threads 14 can be single lead, double lead, or triple lead. The threads 14 allows for the pedicle screw 10 to properly grip the bone of the vertebra. Generally, the gripping force with the bone is strong enough to prevent any loosening from occurring after surgery is performed.

FIGS. 2A-2D show various views of one embodiment of the washer 40. When assembled for use, the washer 40 sits on top of the shaft head 16 and inside the tulip head 60.

In certain embodiments, an inner surface of the washer 40 has a knurled finish 42 to properly lock the washer 40 onto the shaft head 16. The washer 40 can have one or more slots 44 to allow for expansion when the washer 40 is tightly pressed onto the shaft head 16. The washer 40 further has a cut top portion 46, which accommodates the rod when inserted into the patient. In the embodiment shown, the cut top portion 46 is shown as semi-circular, but it is to be understood that such shape will generally conform to the cross-sectional configuration of the rod being inserted into the patient. The washer 40 helps to stabilize the tulip head 60 once the rod compresses onto the washer 40 when inserted into the patient. This action locks the tulip head 60 onto the shaft head 16 and ensures that the tulip head 60 is in a fixed position. The pedicle screw 10 can rotate freely within the washer 40 until such time as the rod is locked in place and held against the cut top portion 46 of the washer 40 by the surgeon inserting the pedicle screw 10 into the patient.

FIGS. 3A-3D show various views of one embodiment of the tulip head 60. When assembled for use, the shaft 12 of the pedicle screw 10 is positioned in the tulip head 60 such that the shaft head 16 of the pedicle screw 10 sits at a bottom portion 62 of the tulip head 60. Such positioning allows the tulip head 60 to move in various rotational directions, providing the pedicle screw 10 with poly-axial movement within the tulip head 60 before being inserted into the patient. The tulip head 60 has a channel 64 along its front surface that allows for the rod to slide into place in the tulip head 60 when inserted into the patient.

Figure 3A:
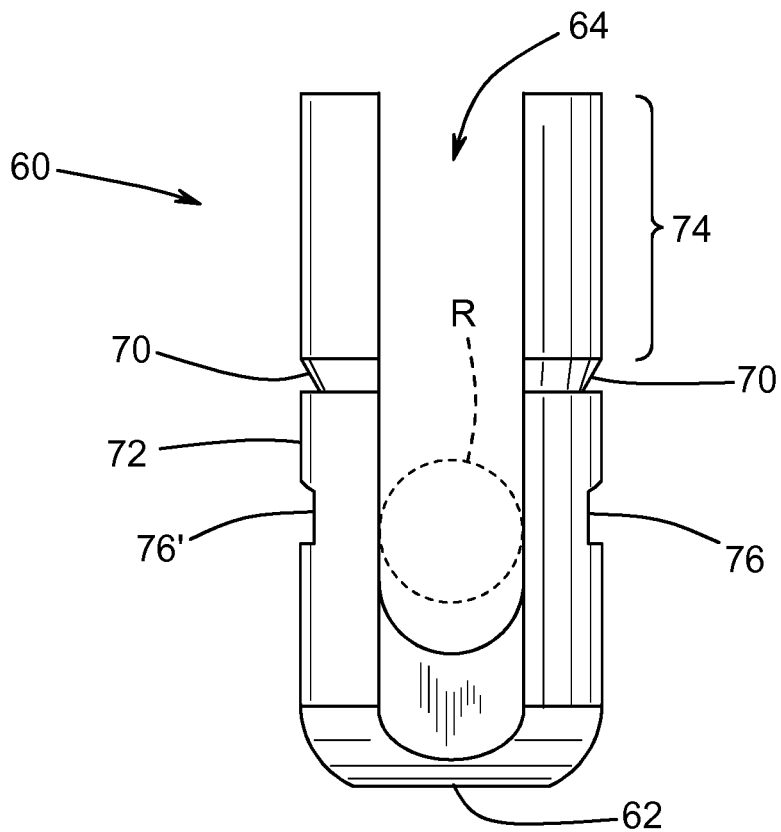
FIG. 3A shows a front view of one embodiment of a tulip head of a pedicle screw assembly.
Figure 3B:
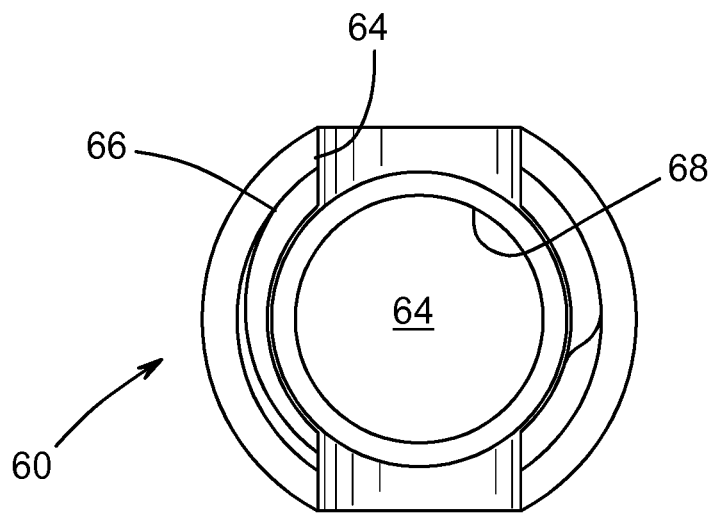
FIG. 3B shows a top view of the tulip head shown in FIG. 3A.
Figure 3C:
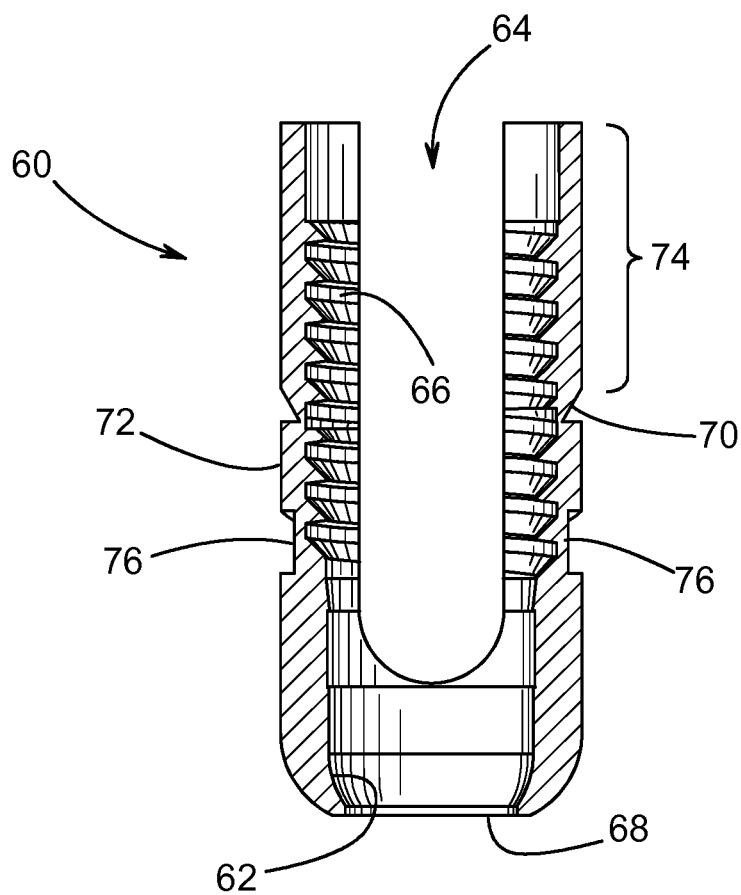
FIG. 3C shows a sectional view of the tulip head shown in FIG. 3A.
Figure 3D:
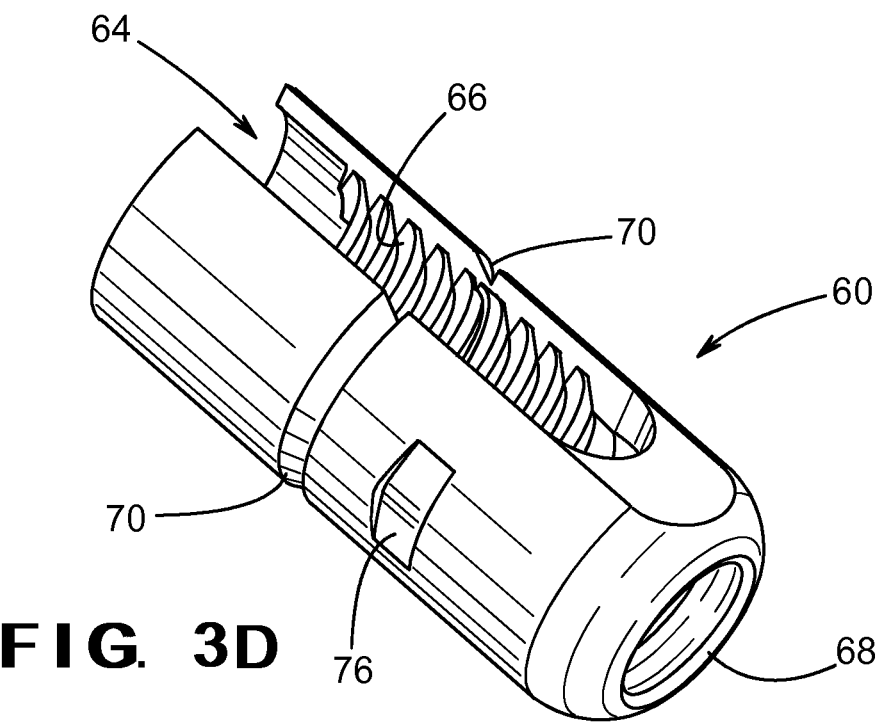
FIG. 3D shows an isometric view of the tulip head shown in FIG. 3A.

The tulip head 60 has internal threads 66 that allow for the set screw 80 to be screwed in to compress the rod against the washer 40 and lock the poly-axial screw 10 into position in the patient. The set screw 80 also functions to keep the rod in place, without any loosening, once the surgery has been performed. As best seen in FIG. 3C, the tulip head 60 can have a circular groove 68 cut on an inner surface of the bottom portion 62 that locks the washer 40 in the tulip head 60. The tulip head 60 can further have at least one circular cut 70 on an outer surface 72 thereof that allows for the surgeon to break off an excess extension portion 74 of the tulip head 60 once fixation within the patient is achieved. In such embodiments, the extension portion 74 facilitates the position of the set screw 80 into the tulip head 60. In certain embodiments, the outer surface 72 of the tulip head 60 has one or more slots 76 and 76' (optionally, on opposing sides of the outer surface 72), which are used to grip the tulip head 60 with a proper surgical instrument and drive the pedicle screw 10 into place.

FIGS. 4A-4C show various views of another embodiment of a tulip head 160. When assembled for use, the shaft 12 of the pedicle screw 10 is positioned in the tulip head 160 such that the shaft head 16 of the pedicle screw 10 sits at a bottom portion 162 of the tulip head 160. Such positioning allows the tulip head 160 to move in various rotational directions, providing the pedicle screw 10 with poly-axial movement within the tulip head 160 before being inserted into the patient. The tulip head 160 has a channel 164 along its front surface that allows for the rod to slide into place in the tulip head 160 when inserted into the patient.

The tulip head 160 has internal threads 166 that allow for the set screw 80 to be screwed in to compress the rod against the washer 40 and lock the poly-axial screw 10 into position in the patient. The set screw 80 also functions to keep the rod in place, without any loosening, once the surgery has been performed. The tulip head 160 can have a groove 168 cut on an inner surface of the bottom portion 162 that locks the washer 40 in the tulip head 160. The tulip head 160 can further have at least one circular cut 170 on an outer surface 172 thereof that allows for the surgeon to break off an excess extension portion 174 of the tulip head 160 once fixation within the patient is achieved. In such embodiments, the extension portion 174 facilitates the position of the set screw 80 into the tulip head 160. In certain embodiments, the outer surface 172 of the tulip head 160 has one or more openings 176 (optionally, on opposing sides of the outer surface 172), which are used to grip the tulip head 160 with a proper surgical instrument and drive the pedicle screw 10 into place.

In the embodiment shown in FIGS. 4A-4C, the tulip head 160 can include one or more transverse cuts 178 at the bottom 162 of the tulip head 160. The transverse cut(s) 178 enhances the shaft's poly-axial movement perpendicular to a central axis of the rod.

Many other variations of the tulip heads described herein are possible. It is to be understood that the tulip head can vary in length. These variations include, but not limited to, having threads on the outside of the tulip head to allow for the insertion of a nut on the outside of the tulip head in order to allow for a larger holding force and adds strength to the tulip wings. Outer threads on the tulip head also allow for a tube to be screwed in on the outside for minimally invasive surgery.

Figure 5A:
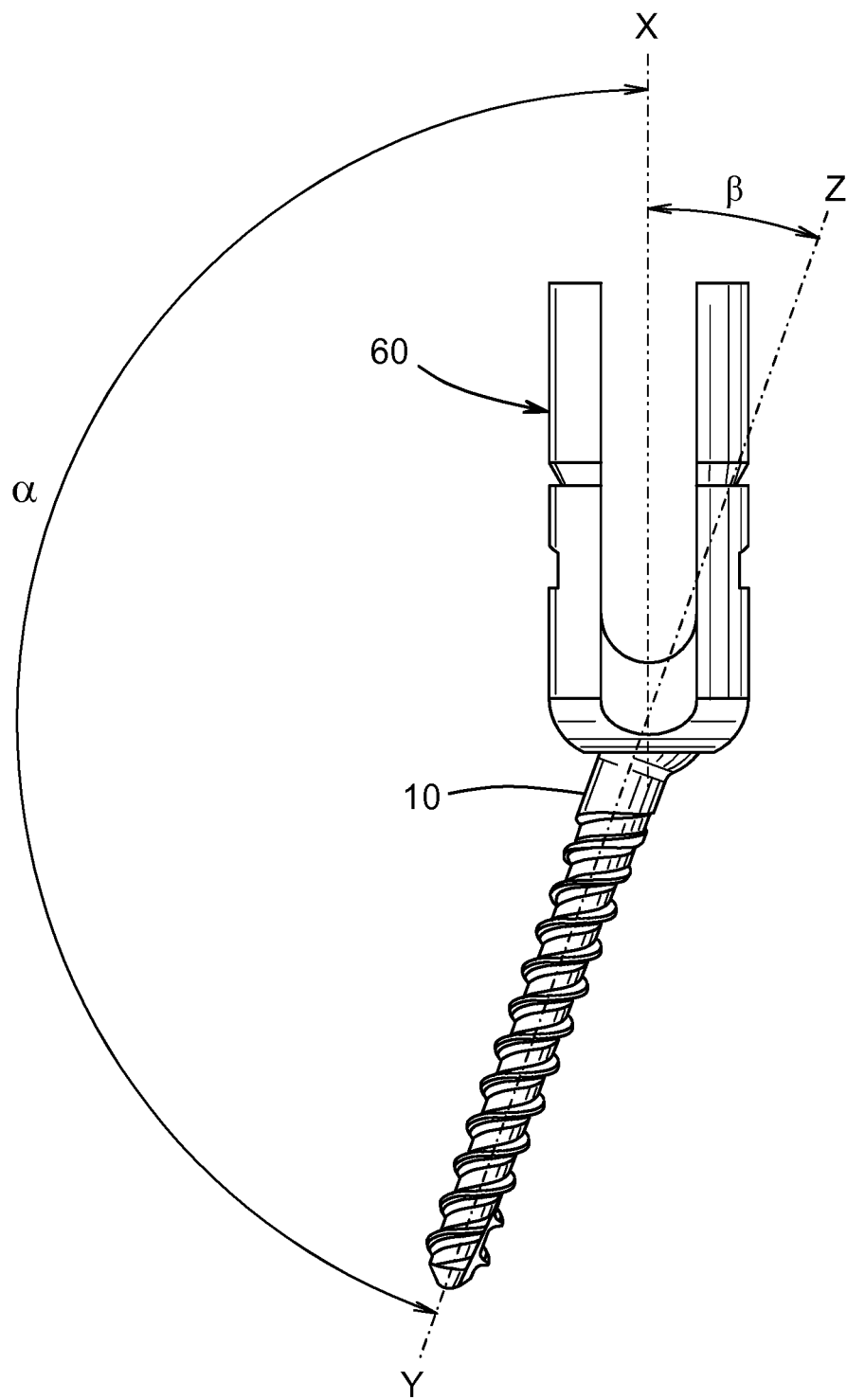
FIG. 5A is an isometric view of the tulip head of FIGS. 3A-3D shown with a poly-axial pedicle screw.

FIG. 5A shows the pedicle screw 10 inserted through the channel 64 and through the bottom opening 68 of the tulip head 60. The bottom opening 68 is configured to allow a distal end of the pedicle screw shaft 12 to rotate freely in a circumferential manner about an X axis defined by the channel in the tulip head. That is, the pedicle screw 10 can circumferentially rotate both in an Y-axis direction about an angle α, and in an Z-axis direction to about an angle β.

Figure 5B:
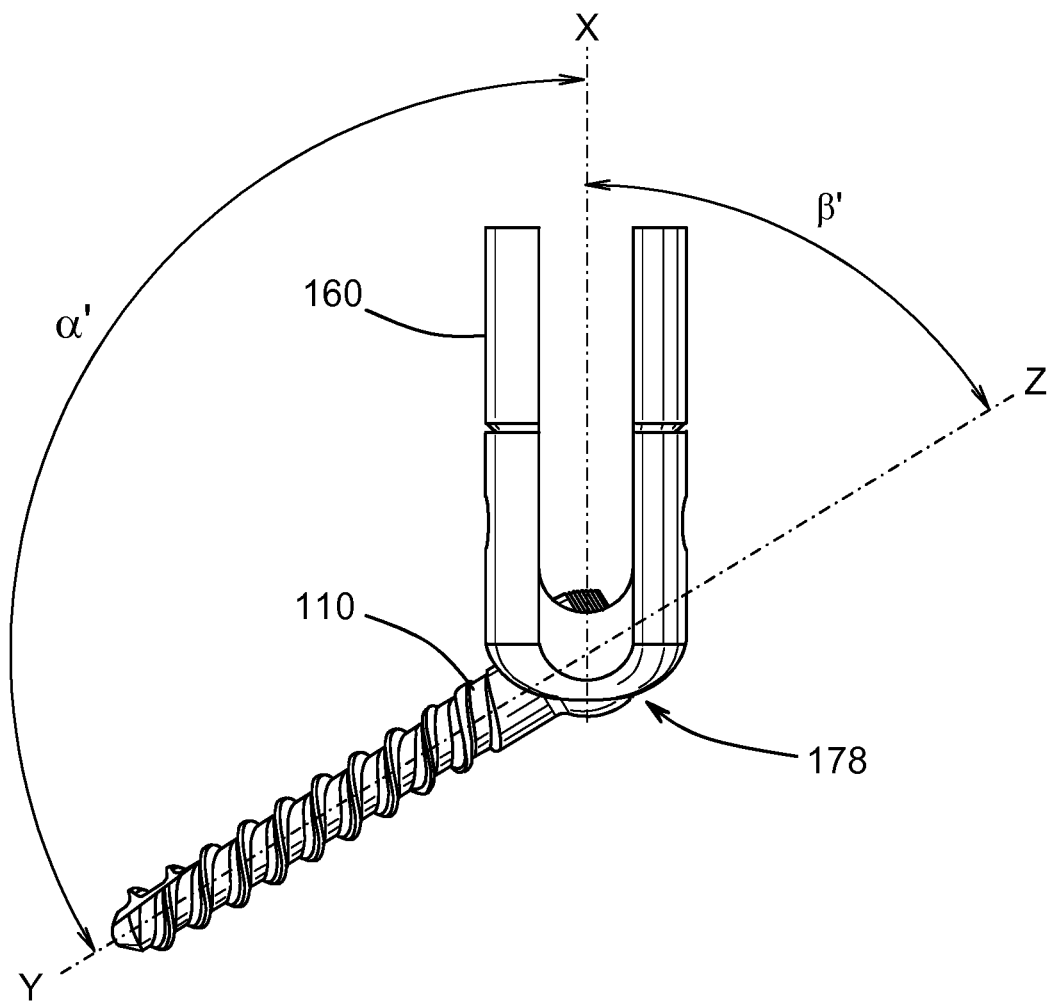
FIG. 5B is an isometric view of the tulip head of FIGS. 4A-4C shown with a poly-axial pedicle screw.
Figure 6A:
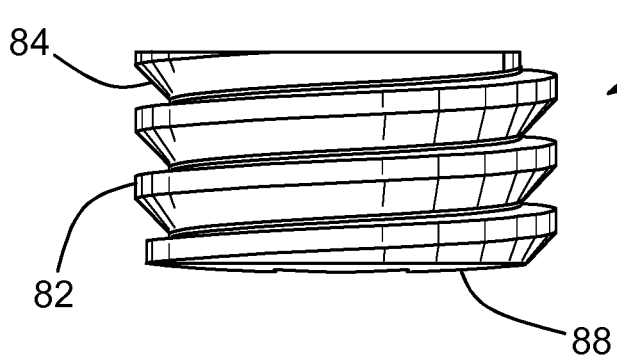
FIG. 6A shows a front view of a set screw of a pedicle screw assembly.
Figure 6B:
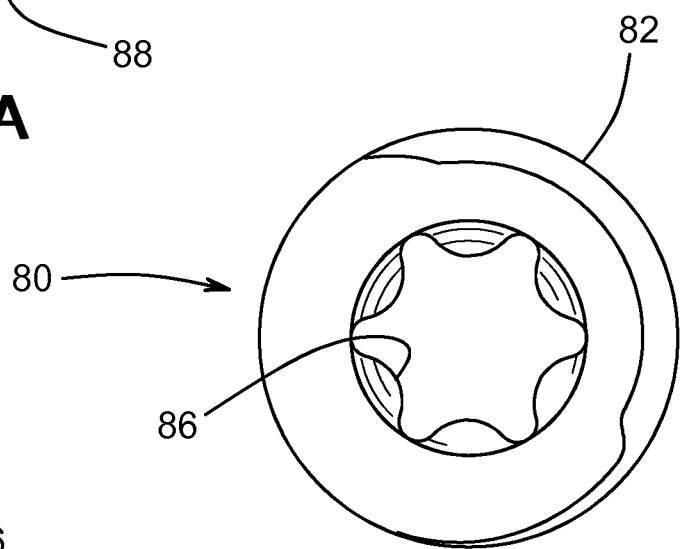
FIG. 6B shows a top view of a set screw of a pedicle screw assembly.
Figure 6C:
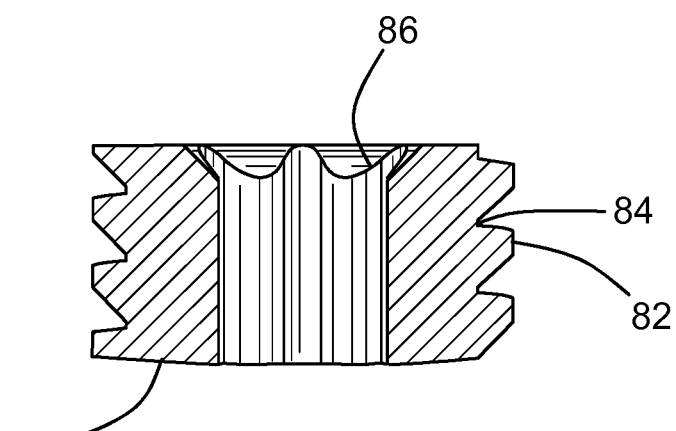
FIG. 6C shows a sectional view of a set screw of a pedicle screw assembly.
Figure 6D:
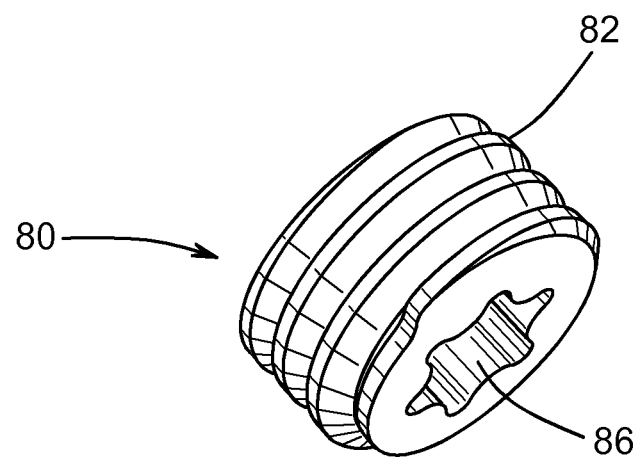
FIG. 6D shows an isometric view of a set screw of a pedicle screw assembly.

FIG. 5B shows the pedicle screw 10 inserted into the channel 164 and through the bottom opening 168 of the tulip head 160 having the transverse cut(s) 178. The pedicle screw 10 can rotate about the Y-axis to about an angle α', and about the Z-axis to about an angle β'. Thus, it can readily be seen that for embodiments where the tulip head 160 includes the transverse cut 178, there is a greater degree of freedom of rotation of the pedicle screw 10.

FIGS. 6A-6D show various views of one embodiment of the set screw 80 which has threads 82 on an outside surface 84. The set screw thread 82 allow the set screw 80 to be inserted into the tulip head 60 and locked in place. When tightened during insertion into the patient, a bottom surface 88 of the set screw 80 presses on top of the rod, which locks the washer 40 onto the shaft head 16 of the pedicle screw 10.

In certain embodiments, the set screw 80 can have a torx cut extrusion 86 on the top. This facilitates a torx driver for use in inserting the set screw 80 into the tulip head 60. However, other geometries, in place of a torx extrusion, can be used on the set screw top and corresponding set screw screwdriver.

FIGS. 7A-7B show various views of the pedicle screw assembly 8 including each of the pedicle screw 10, washer 40, tulip head 60, and set screw 80. When in use, the pedicle screw shaft 12 functions to screw into the vertebral bone and lock itself in the bone. The washer 40 functions to lock the tulip head 60 relative to the pedicle screw 10 once the proper positioning of the tulip head 60 has been determined. This is done by compressing the washer 40 down onto the shaft head 16 of the pedicle screw 10. The tulip head 60 functions to facilitate the set screw 80 and to provide a housing for the rod, washer 40, and pedicle screw head 16. The set screw 80 functions to press the rod against the washer 40, which in turn, locks the pedicle screw assembly 8 in place in the patient. The set screw 80 also provides gripping force against the rod to hold the rod in place without slipping or sliding after insertion into the patient.

Packaging Assembly

The poly-axial pedicle screw assembly 8 can be packaged in one of several packaging assemblies to provide ease of sterilization and ease of access for insertion during surgery. In general, certain packaging assemblies hold the pedicle screw 10, the washer 40, and the tulip head 60 in a packaged manner. In certain embodiments, the packaging assembly includes an extra compartment that holds the set screw 80. In other embodiments, the packaging assembly further holds the set screw 80 in a packaged manner along with the pedicle screw 10, the washer 40, and the tulip head 60.

The packaging assembly allows for the pedicle screw and set screw to sit upright while packaged. This allows for the surgeon to use drivers to grab the pedicle screw and set screw without touching the screws, thereby reducing the risk of infection during surgery.

Figures 8A, 8B:
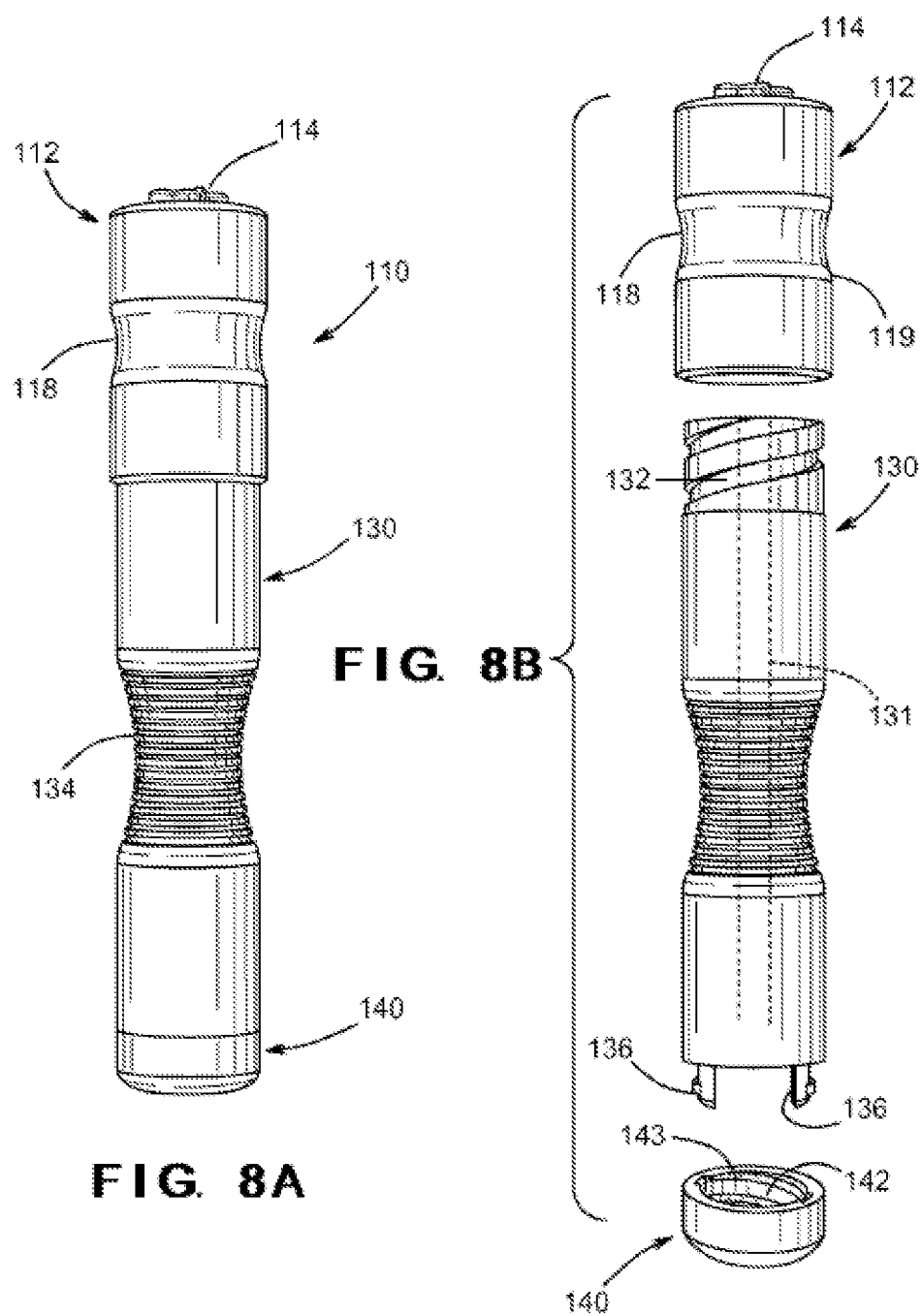
FIG. 8A shows a front view of one embodiment of a packaging assembly having a fastening lock mechanism.
FIG. 8B shows a trimetric (or, unassembled) view of the packaging assembly of FIG. 8A.
Figures 11A, 11B:
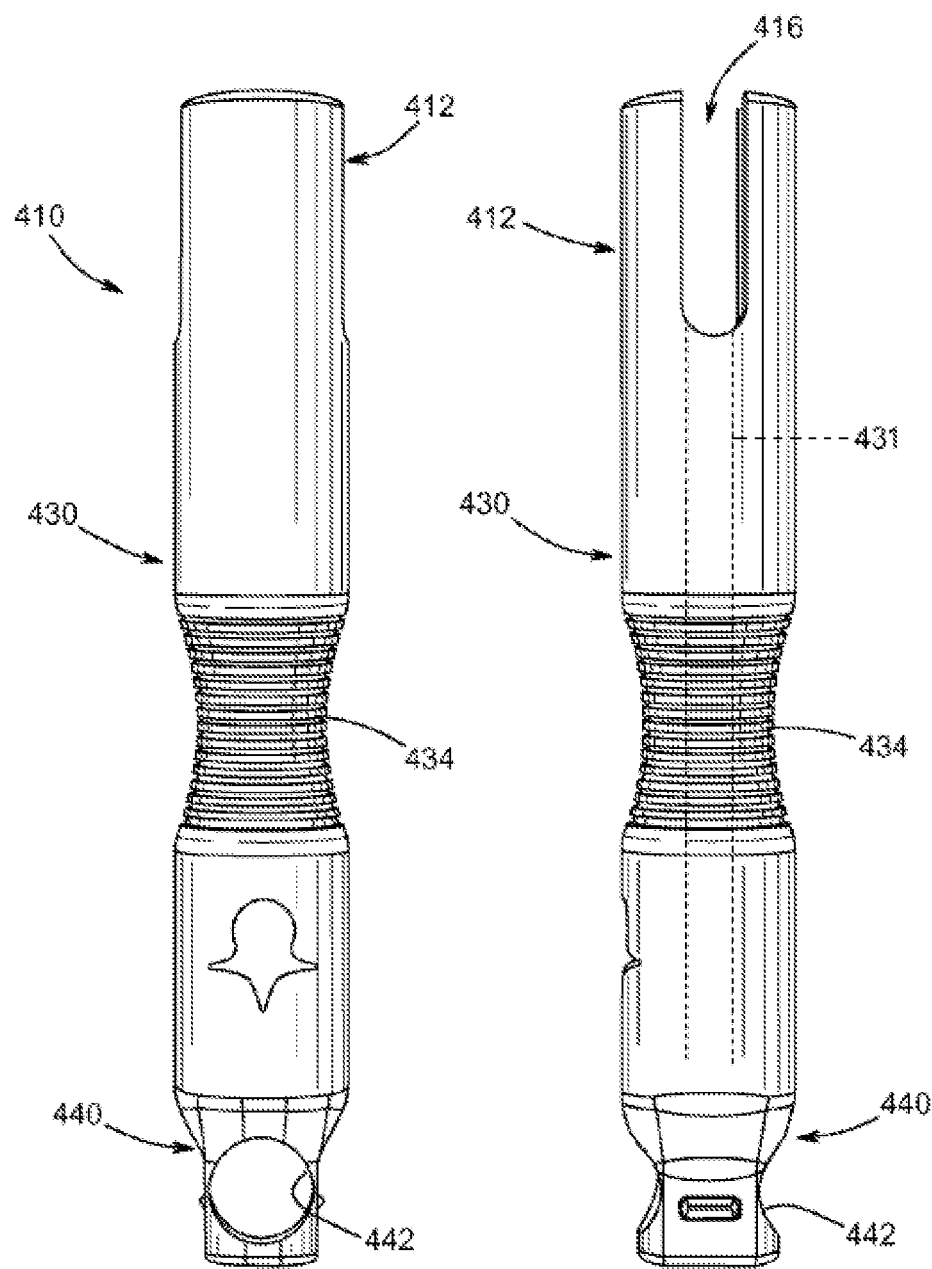
FIG. 11A shows a front view of one embodiment of a 1-part packaging assembly.
FIG. 11B shows a trimetric (or, unassembled) view of the packaging assembly of FIG. 11A.

FIGS. 8A-8B show one embodiment of a fastening lock-type packaging assembly 110 having a cap 112, a body 130, and a bottom compartment 140.

The body 130 generally defines an axially extending opening 131 (shown in phantom in FIG. 8B) which is configured to receive a preassembled pedicle screw 10, washer 40 and tulip head 60/160. The cap 112 can be removably connected to the body 130. The cap 112 can include internal threads or detents (not shown) which can matingly engage external threads 132 on a top portion of the body 130. The skilled person will recognize that the curvature and knurled surfaces of the cap 112 and body 130 can vary significantly in design.

In certain embodiments, the cap 112 includes an opening 114 on the top which allows for a sterilization gas to access the pedicle screw, the washer and the tulip head within the body 130. The cap 112 can also have a curvature 118 which, along with knurls 119, allows for the surgeon to grasp the cap 112 for removal from the body 130.

The body 130 can have a curved and knurled outer surface 134. This type of outer surface allows for the surgeon to better grip the body of the packaging assembly 110 during surgery. Furthermore, the packaging assembly 110 can vary in shape. For instance, the packaging assembly 110 can have a square body or any other polygonal-shaped geometry.

The bottom compartment 140 can be removably affixed to a bottom of the body 130. The body 130 can include flanges 136 that can engage an inner surface 142 of the bottom compartment 140, when assembled. The inner surface 142 of the bottom compartment 140 can define a chamber 143 that is configured to hold the set screw 80 for easy removal when needed. In another alternative embodiment, the set screw compartment is located on the top instead of bottom of the packaging assembly 110.

In general, the pedicle screw, washer and tulip head sit upright in the packaging assembly 110, which allows the surgeon to grab the pre-assembled pedicle screw, washer, and tulip head from the body 130 with the screwdriver without ever coming into contact with the pedicle screw itself. This results in a decreased chance of patient infection. The same is true for the set screw, which the surgeon can grab out of the bottom compartment 140 without ever coming into contact with the set screw 80 itself.

FIGS. 9A-9B show one embodiment of a snap-fit lock-type packaging assembly 210 having a cap 212, a body 230, and a bottom compartment 240.

The body 230 generally defines an axially extending opening 231 (shown in phantom in FIG. 9B) which is configured to receive a preassembled pedicle screw 10, washer 40 and tulip head 60/160. The cap 212 can be removably connected to the body 230 with detents 216 which can matingly engage flanges 232 on a top portion of the body 230. The skilled person will recognize that the curvature and knurled surfaces of the cap 212 and body 230 can vary significantly in design. By way of non-limiting example, the packaging assembly 210 can have a tight-fit feature that allows the surgeon to pull off the cap 212 and bottom compartment 240 only with a certain amount of force.

In certain embodiments, the cap 212 includes an opening 214 on the top which allows for a sterilization gas to access the pedicle screw, the washer and the tulip head within the body 130. The cap 212 can also have a curvature 218 which, along with knurls 219, allows for the surgeon to grasp the cap 212 for removal from the body 230.

The body 230 can have a curved and knurled outer surface 234. This type of outer surface allows for the surgeon to better grip the body of the packaging assembly 210 during surgery. Furthermore, the packaging assembly 210 can vary in shape. For instance, the packaging assembly 210 can have a square body or any other polygonal-shaped geometry. In another alternative embodiment, the set screw compartment is located on the top instead of bottom of the packaging assembly 210.

The bottom compartment 240 can be removably affixed to a bottom of the body 230. The body 230 can include flanges 236 that can engage an inner surface 242 of the bottom compartment 240 when assembled. The inner surface 242 of the bottom compartment 240 can define a chamber 244 that is configured to hold the set screw 80 for easy removal when needed.

In general, the pedicle screw, washer and tulip head sit upright in the packaging assembly 210, which allows the surgeon to grab the pre-assembled pedicle screw, washer and tulip head from the body 230 with the screwdriver without ever coming into contact with the pedicle screw itself. This results in a decreased chance of patient infection. The same is true for the set screw, which the surgeon can grab out of the bottom compartment 240 without ever coming into contact with the set screw itself.

FIGS. 10A-10B show one embodiment of a packaging assembly 310 having a cap 312, and a body 330.

The body 330 generally defines an axially extending opening 331 (shown in phantom in FIG. 10B) which is configured to receive a preassembled pedicle screw 10, washer 40, and tulip head 60/160. The cap 312 can be removably connected to the body 330 by matingly engaging a top portion of the body 330. The skilled person will recognize that the curvature and knurled surfaces of the cap 312 and body 330 can vary significantly in design. By way of non-limiting example, the packaging assembly 310 can have a tight-fit feature that allows the surgeon to pull off the cap 312 only with a certain amount of force.

In certain embodiments, the cap 312 includes a set screw storage compartment 340 near the top which allows for the removable insertion of the set screw 80. The set screw storage compartment 340 can have radially extending walls 344 that allow for easy access to sides of the set screw 80 for easy removal by the surgeon. Also, in certain embodiments, the cap 312 can include an opening 314 on the top which allows for a sterilization gas to access the pedicle screw, the washer and the tulip head within the body 130.

The cap 312 can also have a curvature 318 which, along with knurls 319, allows for the surgeon to grasp the cap 312 for removal from the body 330.

The body 330 can have a curved and knurled outer surface 334. This type of outer surface allows for the surgeon to better grip the body of the packaging assembly 310 during surgery. Furthermore, the packaging assembly 310 can vary in shape. For instance, the packaging assembly 310 can have a square body or any other polygonal-shaped geometry. In another alternative embodiment, the set screw compartment is located on the top instead of bottom of the packaging assembly 310.

In general, the pedicle screw, washer and tulip head sit upright in the packaging assembly 310, which allows the surgeon to grab the pedicle screw, washer and tulip head with the screwdriver without ever coming into contact with the pedicle screw itself. This results in a decreased chance of patient infection. The same is true for the set screw, which the surgeon can grab out of the cap compartment 340 without ever coming into contact with the set screw itself.

FIGS. 11A-11D show one embodiment of a packaging assembly 410 having a central body portion 430 having a channel portion 412 at a first end and a screw set compartment 440 at a second end.

The body 430 generally defines an axially extending opening 431 (shown in phantom in FIG. 11B) which is configured to receive a preassembled pedicle screw 10, washer 40 and tulip head 60/160. The skilled person will recognize that the curvature of the body portion 430 can vary significantly in design. The body 430 can have a curved and knurled outer surface 434. This type of outer surface allows for the surgeon to better grip the body of the packaging assembly 410 during surgery. Furthermore, the packaging assembly 410 can vary in shape. For instance, the packaging assembly 410 can have a square body or any other polygonal-shaped geometry. In another alternative embodiment, the set screw compartment is located on the top instead of bottom of the packaging assembly 410.

The screw compartment 440 can be defined by walls 442 which allow for the removable insertion of the set screw. In general, the pedicle screw, washer and tulip head sit upright in the packaging assembly 410, which allows the surgeon to grab the pre-assembled pedicle screw, washer and tulip head with the screwdriver without ever coming into contact with the pedicle screw itself. This results in a decreased chance of patient infection.

The channel portion 412 of the body can have opposing walls 414 which define a packaging channel 416. In the embodiment shown, the packaging channel 416 has substantially the same configuration as the channel 164 defined by the tulip head 60/160. As best seen in FIGS. 11C-11D, the channel portion 412 includes a lip or edge 418 which extends radially inwardly from inner walls 414. The edge 418 matingly receives the bottom 62/162 of the tulip head 60/160.

In the embodiment shown in FIGS. 12A-12B, the packaging assembly 410 can include a sleeve 512 made of a suitable material that substantially prevents any contamination of the tulip head 60/160 when being slidably removed from the channel portion 412 of the packaging assembly 410. The sleeve 512 has opposing walls which define a sleeve channel 516 which have substantially the same configuration as the channel 64/164 defined by the tulip head 60/160.

Also, in the embodiment shown in FIGS. 12A-12B, the packaging assembly 410 can further include a sleeve 612 made of a suitable material that substantially prevents any contamination of the set screw when being removed from the screw compartment 440 of the packaging assembly 410. The sleeve 612 has walls which define a screw sleeve channel 616 which have substantially the same configuration as the screw compartment 440.

Pedicle Screw Screwdriver Assembly

Figure 13A:
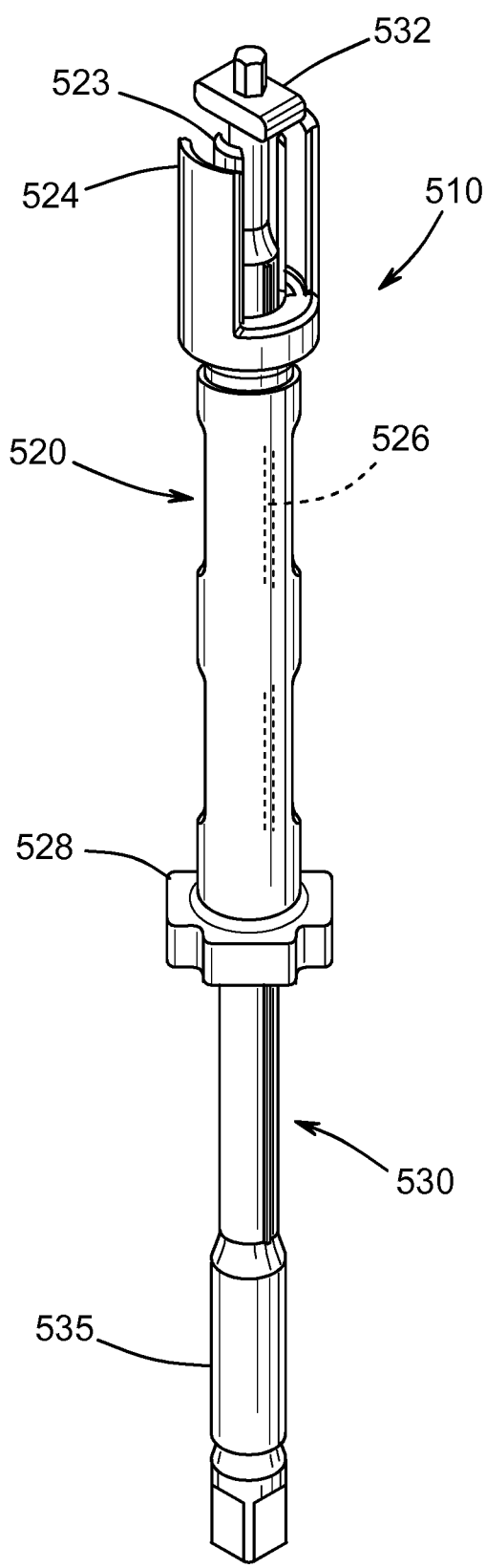
FIG. 13A shows an isometric view of a pedicle screw screwdriver assembly in a first position.
Figure 13B:
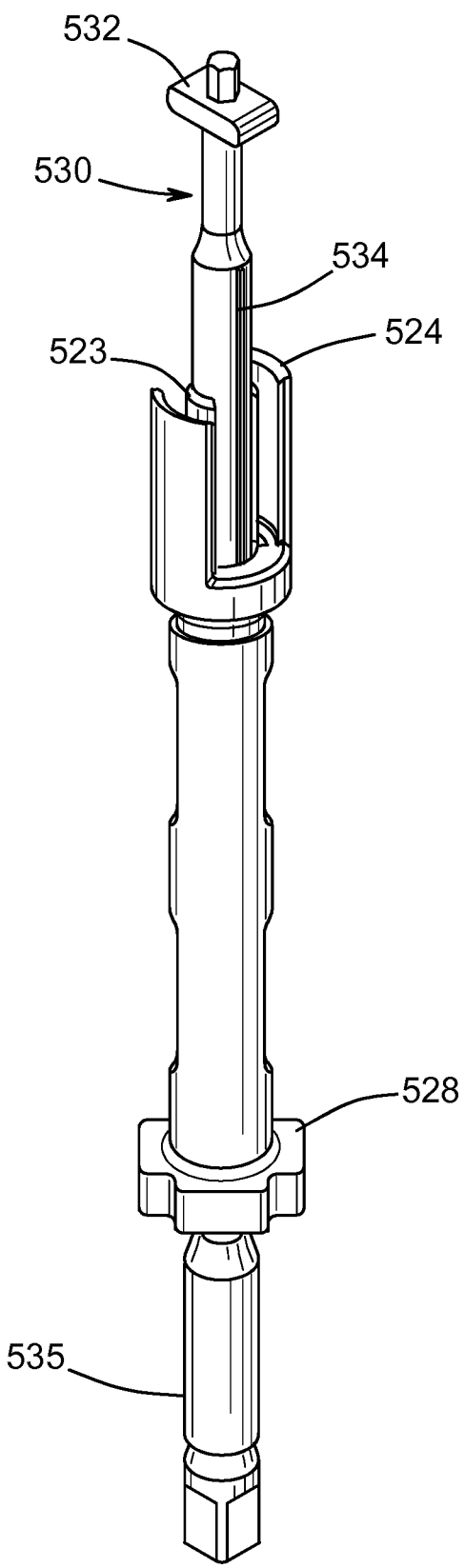
FIG. 13B shows an isometric view of a pedicle screw screwdriver assembly in a second position.

The pedicle screw assembly 8 can be inserted into the patient using a suitable tool, such as, for example a pedicle screw screwdriver assembly 510 shown in FIGS. 13A-13B. In general, the pedicle screw screwdriver assembly 510 includes a sleeve 520 and a driver 530 which are in a coaxial relationship and which can move in an axial direction with respect to each other. The sleeve 520 slides up and down without any rotational movement relative to the driver 530. This allows the surgeon to grasp the pedicle screw, implant the device, and then release the holding force by pulling up the sleeve 520.

The sleeve 520 can have inner wings 523 and outer wings 524, which allow for gripping of the tulip head on the outside and inside. This enables the surgeon to grab the pedicle screw out of the packaging and then implant the pedicle screw without worrying about the pedicle screw failing.

The driver 530 has an extrusion 532 on the top. The size of this extrusion 532 generally matches the size of the opening of the tulip head. The extrusion 532 facilitates the tulip head 60 rotating along with the shaft when performing surgery. The extrusion 532 also adds extra gripping force between the driver 530 and the tulip head 60.

In certain embodiments, the sleeve 520 has cuts 526 along in inner surface (shown in phantom) of the sleeve 520. The sleeve 520 further has a "plus"-shaped extrusion 528, which allows for the surgeon to properly grasp the sleeve 520 to pull up or push down.

The outside of the driver 530 also has a small extrusion 534 that matches the cut 526 on the inside of the sleeve 520. The matching extrusion 534 and cut 526 allow for the sleeve 520 to slide up and down along the driver 530 without there being any relative rotation between the sleeve 520 and driver 530. By pushing the sleeve 520 up (as shown in FIG. 13A), the surgeon can grasp the poly-axial pedicle screw, and by pulling the sleeve 520 down (as shown in FIG. 13B), the surgeon can release the gripping force once he or she has implanted the pedicle screw.

In certain embodiments, the driver 520 can have a specific base shape 535 that matches a standard surgical ratcheting handle. However, the specific shape of the driver base 535 can vary.

Set Screw Screwdriver Assembly

Figure 14C:
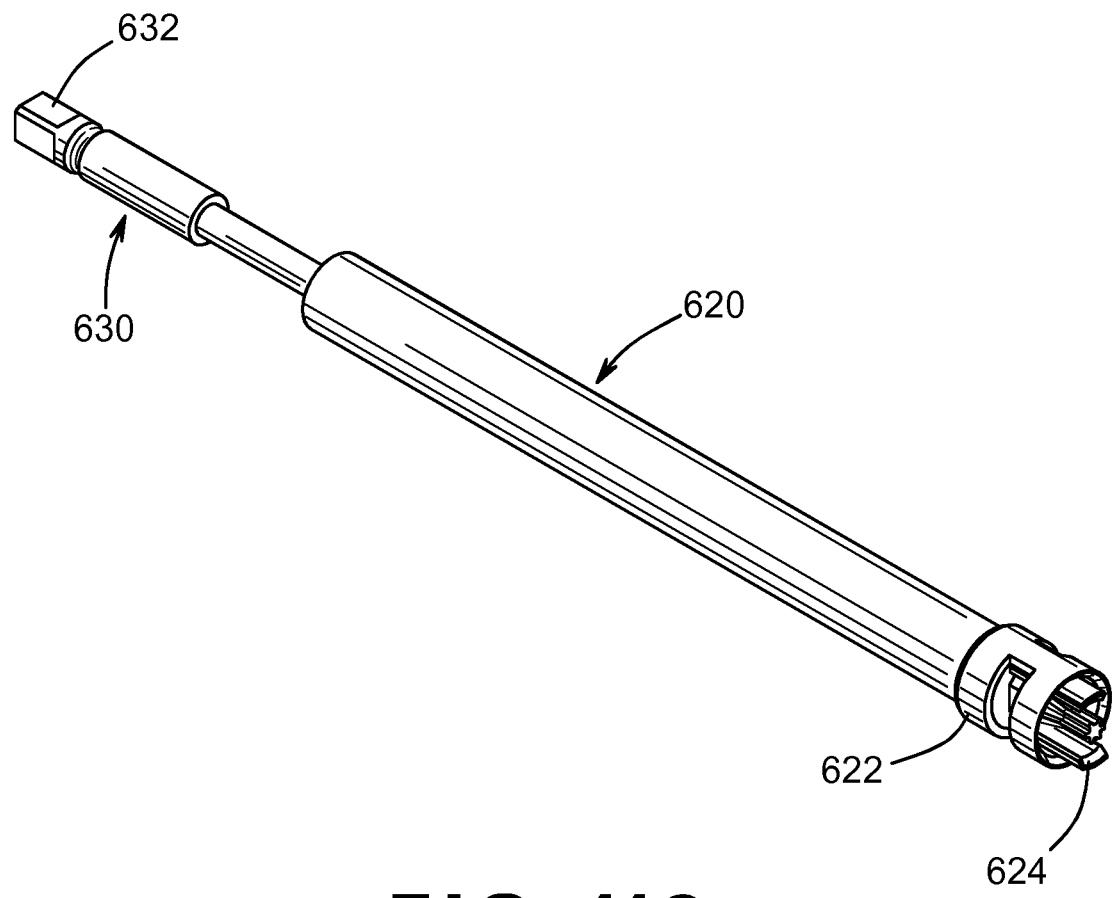
FIG. 14C shows an isometric view of a set screw screwdriver assembly.

The set screw 80 can be inserted into the patient using a suitable tool, such as, for example, a set screw screwdriver assembly 610 shown in FIGS. 14A-14C. In general, the set screw screwdriver assembly 610 includes a sleeve 620 and a driver 630 which are in a coaxial relationship and which can move in an axial direction with respect to each other. The set screw screwdriver assembly 610 allows the surgeon to grasp the set screw, tighten the set screw, and then release the holding force by pulling up the sleeve.

The top of the sleeve 620 has cuts 622 for proper placement of the set screw inside the tulip head. The top of the sleeve 620 also has wings 624 that grip onto the outside of the set screw. This allows the surgeon to grab the set screw and insert it without actually touching the set screw itself.

The driver 630 has a torx head 632 which matches the geometry of the cut of the set screw. As with the set screw, it should be understood that this geometry can vary.

The set screw screwdriver assembly operates in a manner similar to the pedicle screw screwdriver assembly in that the sleeve 36 can slide up and down without any rotational movement relative to the driver 37.

Though certain embodiments of the spinal fixation assembly disclosed herein are specified, it should be understood that these embodiments are given by way of illustration only. From the above discussion, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular element or material to the teachings of the disclosure without departing from the essential scope thereof.

What is claimed is:

1. A combined assembly of a packaging assembly and a sterile medical component comprising:
   a packaging assembly including:
      a hollow body including an inner wall that defines an interior space extending completely through the hollow body, the inner wall having an edge that extends inwardly from the inner wall into the interior space, and
      a cap that is supported on the body and encloses the interior space; and
   a sterile medical component disposed within the interior space of the hollow body in engagement with and directly supported on the edge that extends inwardly from the inner wall into the interior space.

2. The combined assembly defined in claim 1 wherein the hollow body is cylindrical in shape, and wherein the edge extends radially inwardly from the inner wall into the interior space.

3. The combined assembly defined in claim 1 wherein the cap is removably supported on the body.

4. The combined assembly defined in claim 3 wherein the cap includes an internal thread that engages an external thread provided on the body to removably support the cap on the body.

5. The combined assembly defined in claim 3 wherein the cap includes a detent that engages a flange provided on the body to removably support the cap on the body.

6. The combined assembly defined in claim 3 wherein the body has a curved outer surface.

7. The combined assembly defined in claim 6 wherein the cap has a curved outer surface.

8. The combined assembly defined in claim 3 wherein the body has a curved and knurled outer surface.

9. The combined assembly defined in claim 8 wherein the cap has a curved and knurled outer surface.

10. The combined assembly defined in claim 1 wherein the cap includes an opening therethrough that is adapted to allow a sterilization gas to pass therethrough into the interior space of the hollow body.

11. The combined assembly defined in claim 1 wherein the hollow body includes a first end and a second end, the cap is supported on the first end of the body, and a compartment is supported on the second end of the hollow body and defines a chamber.

12. The combined assembly defined in claim 11 wherein the compartment is removably supported on the second end of the hollow body.

13. The combined assembly defined in claim 12 wherein the compartment includes an inner surface that engages a flange provided on the body to removably support the compartment on the second end of the hollow body.

14. The combined assembly defined in claim 12 wherein the compartment includes a detent that engages a flange provided on the body to removably support the compartment on the second end of the hollow body.

* * * * *